US006910050B2

(12) United States Patent  
Pawlick

(10) Patent No.: US 6,910,050 B2
(45) Date of Patent: Jun. 21, 2005

(54) ANIMAL CARE REGISTRY SYSTEM AND METHOD

(76) Inventor: Harvey Gustave Pawlick, P.O. Box 6467, Napa, CA (US) 94581

( * ) Notice: Subject to any disclaimer, the term of this patent is extended or adjusted under 35 U.S.C. 154(b) by 119 days.

(21) Appl. No.: 10/436,141

(22) Filed: May 13, 2003

(65) Prior Publication Data

US 2004/0230607 A1 Nov. 18, 2004

(51) Int. Cl.$^7$ .............................................. G06F 17/30
(52) U.S. Cl. ...................... 707/104.1; 707/102; 379/67; 40/631; 434/154
(58) Field of Search ........................... 707/3, 10, 104.1, 707/102; 379/67; 40/299, 300; 340/573; 640/20; 342/357.07; 434/154; 705/1–10; 283/70

(56) References Cited

U.S. PATENT DOCUMENTS

| | | | | |
|---|---|---|---|---|
| 4,091,766 | A | * | 5/1978 | Colliard ...................... 359/518 |
| 4,650,219 | A | * | 3/1987 | Sigman ....................... 283/70 |
| 5,036,610 | A | | 8/1991 | Fehr ............................. 40/300 |
| 5,369,900 | A | * | 12/1994 | Garrison ...................... 40/631 |
| 5,726,884 | A | * | 3/1998 | Sturgeon et al. ............... 705/9 |
| 5,878,116 | A | | 3/1999 | Scott ........................ 379/67.1 |
| 6,183,258 | B1 | * | 2/2001 | Cobb et al. .................. 434/154 |
| 6,463,441 | B1 | * | 10/2002 | Paradies ..................... 707/102 |
| 6,748,400 | B2 | * | 6/2004 | Quick ..................... 707/104.1 |
| 2002/0116360 | A1 | | 8/2002 | Meadows |
| 2004/0019609 | A1 | * | 1/2004 | Orton et al. ............. 707/104.1 |

OTHER PUBLICATIONS

Companion Animal Recovery. Web page [online]. American Kennel Club, Inc. [retrieved on May 26, 2003]. Retrieved from the Internet: <URL: http://www.akccar.org/>.

Homeagain MicrochipIdentification System. Web page [online]. HomeAgain, Inc. [retrieved on May 26, 2003]. Retrieved from the Internet: <URL: http//www.homeagain-id.com/>.

'Central Animal Records becomes the first registry approved by Domestic Animal Registries Inc.' Web page [online]. Central Animal Records (Aust) Pty.Ltd [retrieved on May 19, 2003]. Retrieved from the Internet: <URL: http//www-.car.com.au/press/PR_DARRelease.asp>.

'Welcome to the National Dog Registry Web'. Web page [online]. National Dog Registry [retrieved on 200305–19]. Retrieved from the Internet: <URL: http://www.natldogregistry.com/REGISTER.html>.

'*One click and they're home!*'. Web page [online]. AWOL-PET.com, [retrieved on May 19, 2003]. Retrieved from the Internet <URL: http://awolpet.com/whoweare.asp>.

'The World Leader in Pet Identification and Information'. Web page [online]. MyPetID, Inc. [retrieved on May 26, 2003]. Retrieved from the Internet: <URL http://www.mypetid.ca/>.

* cited by examiner

*Primary Examiner*—Shahid Alam
(74) *Attorney, Agent, or Firm*—Stevens, Davis, Miller & Mosher, L.L.P.

(57) ABSTRACT

An animal registry system and method utilizing information either borne by an animal or obtained from the normal abode of the animal to obtain veterinarian, search and/or rescue, concierge and other services to the animal with payment guaranteed to the provider of the services. The animal registry system is operatively connected to a communication system providing an automated response to incidents involving the registered animal.

20 Claims, 20 Drawing Sheets from FIG. 2a

5. Continuing Contact and Support 240

Reaching out to Vets/Animal Businesses
1. Offers for training, display materials, etc.
2. Regularly asking how the service is working and how it can be improved
3. Reaching out to employees, with offers of support, training, materials, plus prizes/rewards Reaching out to Animal Owners 242
1. Newsletter and follow-up calls
2. Remind owners of their animal's value, and our role in protecting that value
3. Upselling new features and services

6. Incident Processing and Tracking 250

Animal Owner Reports Missing or Lost Animal 251
1. Report entered in database using numbers/letters/codes/names
2. Automatic filing with any and all related lost animal databases around the country
3. Automatic notification of all regional animal shelters that a wanted animal is lost--and there's a reward
4. Automatic call-back to animal owner to inquire if animal has returned Third Party Finds Registered Animal 252
1. Finder contacts Registry by phone or Internet
2. Registry takes contact information, ascertain animal's condition and ask finder to wait XXX minutes for owner to call to arrange pickup.
3. Registry automatically notifyies animal owner and supplies all contact information.
4. If finder can't wait, animal is injured or owner doesn't respond within XXX minutes, finder is advised, for a reward, to take animal to closest or most convenient vet.
5. Vet contacts us (phone/fax/Internet), payment is assured, registry contacts owner with animal's location and condition. Finder's reward is approved for payment.
6. Animal owner calls vet to arrange pickup and payment.
7. If owner doesn't contact veterinarian within a reasonable (tbd) time, Registry faxes vet a guarantee of payment.
8. Automatic incident report closing, all databases are notified that the animal was found
9. Animal Control Officers, Special organization/citations/rewards Third Party Delivers Animal to Vet 253
1. Vet contacts Registry, Registry contacts owner with animal's location and condition
2. Animal owner calls vet to discuss condition, treatment, payment and pickup
3. Animal owner pays vet at pickup
4. Automatic incident report closing, all databases notified that animal animal was found Special Care for Extended Missing Periods
- Members handbooks and Internet site have info on what animal owners can do to help recover their animals
- Automatic calling of animal owner to let them know we're still on the job 254

Concierge Services 255
Higher-end, higher-price services as need develops.
- Counselors available to help owners launch a missing animal campaign
- Counselors help with the emotional stress
- Registry arranges pickup of lost animal from Finder or Vet
- Advanced technologies will allow us to notify animal animal owners the moment their animal leaves their home or yard
- Satellite tracking of lost animal
- For ill or very valuable animals, vital signs or other information can regularly be transmitted to owner, vet or trainer
- Animal private investigation services
- Bonded program to counter unlawful actions against registered animals.
- 900 (charge to caller) Telephone Counseling and other Services to FIG. 2c

Fig. 2b

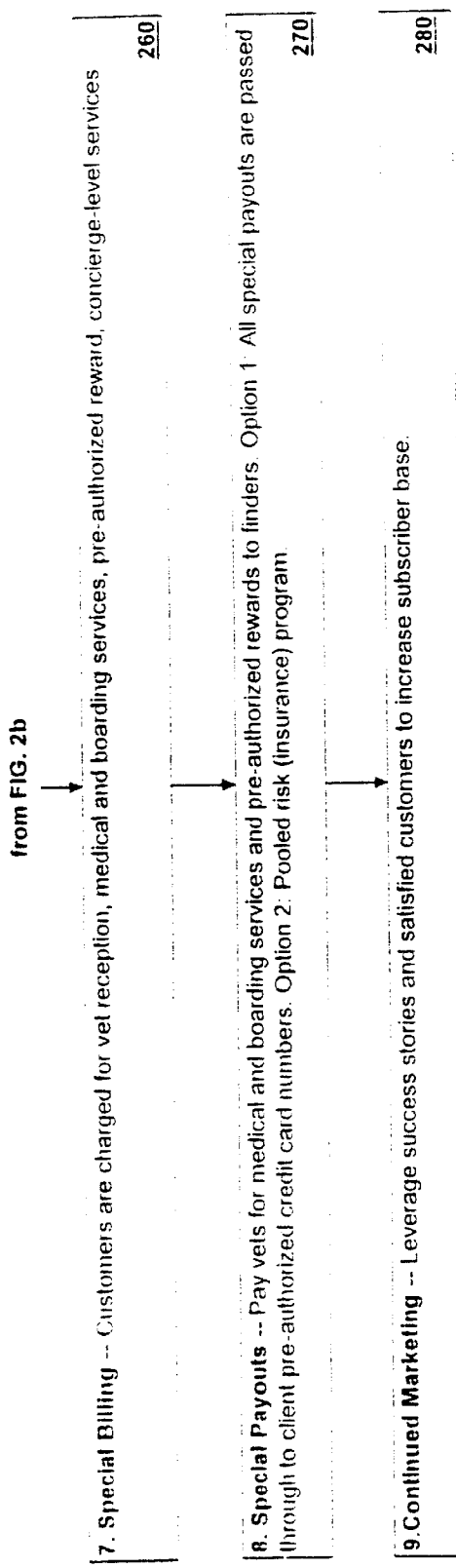

```
                  Registrant Communication Tree:
                Registered Animal Owner Contacts Registry
            (Communication Methods and means include but are not limited to:
      Website/Internet, television broadcast/cable, fiber optic equipment, computer, telephone, facsimile,
      pager, cell phone, two-way/FM/AM/short wave radio, microwave device, US Postal Service, private
      postal/delivery services, private messenger, email equipment, PDA (Personal Digital/Data Assistant),
              other Internet equipment and Website equipment, code, satellite.)
                                        │
                                        ▼
                        Short Welcome Message, then:
    Select Option 1 to report a lost animal, Option 2 to report a lost animal has been found, or Option 3 to
                              check the status of a lost animal.

Opiton 1                    Option 2                      Option 3
       ▼                           ▼                             ▼
    see FIG. 3a               see FIG. 3b              Please input code for  ◄──┐
                                                      missing animal    300      │
                                                               │                 │
                                                               ▼            No   │
                                                       Contactor inputs code.    │
                                                      System reads it back, asks ┤
                                                         for confirmation.       │
                                                      If wrong, repeats process. │ No
                                                               │                 │
                                                              Yes                │
                                                               ▼                 │
                                                      System checks to see if    │
                                                       that animal has been      │
                                                        reported missing.        │
                                                      If wrong, repeats process. ┘   ( DB    )
                                                              310                    ( process)
                                                                                     (   E    )
                                                              Yes                    ( DB    )
                                                               ▼                     ( process)
                                                       System Reads status:          (   F    )
                                                         Missing: yes/no
                                                    Reported missing: date, time, who
                                                     First Contact, date, time, who
                                                    Vet Contact, date, time, who, etc.
                                                              330
                                                               ▼
                                                   System offers option for status of
                                                Yes    another lost animal.   340
                                                               No
                                                               ▼
         Referral is made.      ◄───              System offers option to talk to an
                                       Yes              animal counselor.
                                                               No
                                                               ▼
         └──────────────────────────────►  ( Thank you and goodbye.   350 )
```

Fig. 3c

These database processes are detailed steps that expand on selected Fig. 3a, 3b and 3c flowchart boxes.

Database Process A
1. Search Animal database to see if the number is real.
2. Search Incident database to see if animal has already been reported missing.
3. If already missing, give status report-when reported missing (date and time), who reported it, and zip, etc.

Database Process B
1. Create Incident record (if needed)
2. Record date, time, animal code, caller's name, zip
3. Using animal code as key, look up customer code in animal database, then get customer info from customer database.
4. Notify all appropriate databases that animal is missing.

Database Process C
1. Looks up animal code in Incident database.

Database Process D
1. Inputs found time and date, finder name into Incident database.
2. Marks incident closed
3. Notifies all appropriate databases that the animal is no longer missing.

Database Process E
1. Searches Incident database for animal code.

Database Process F
1. Gives complete status report on the incident, including all dates, times, zips and names involved.

Fig. 3d

```
                Non-Registrant Communication Tree:
         Someone Other Than a Registered Animal Owner Contacts Registry
         (Communication Methods and means include but are not limited to:
   Website/Internet, television broadcast/cable, fiber optic equipment, computer, telephone, facsimile,
   pager, cell phone, two-way/FM/AM/short wave radio, microwave device, US Postal Service, private
   postal/delivery services, private messenger, email equipment, PDA (Personal Digital/Data Assistant),
               other Internet equipment and Website equipment, code, satellite.)
```

Short Welcome Message, then:
Select Option 1 to report a found animal, Option 2 if you are a vet, or Option 3 if you are an animal control officer.

| Option 1 | Option 2 | Option 3 |
|---|---|---|
| see FIG. 4a | Please input code for found animal. 400 | see FIG. 4c |

Contactor inputs code.
System asks for confirmation.
If wrong, repeats process.

↓ Yes

System checks to see if that animal has been reported missing.
If wrong, repeats process. 410

→ DB process J

↓ Yes

Thank you.
The animal brought to you is protected and covered by the Registry.
You will be paid your standard fees for emergency medical care and boarding until the owner can arrange for pick up.

↓

System has Contactor input phone # (with error checking) and name. 420
→ DB process K

↓

The owner will contact you about retrieval.
Enter your Fax # for complete billing and contact info. (with error checking). 450
→ DB process L

↓

Thank you and goodbye. 460

Fig. 4b

```
┌─────────────────────────────────────────────────────────────────────┐
│   Non-Registrant Communication Tree:                                │
│   Someone Other Than a Registered Animal Owner Contacts Registry    │
│   (Communication Methods and means include but are not limited to:  │
│   Website/Internet, television broadcast/cable, fiber optic equipment, computer, telephone, facsimile, │
│   pager, cell phone, two-way/FM/AM/short wave radio, microwave device, US Postal Service, private │
│   postal/delivery services, private messenger, email equipment, PDA (Personal Digital/Data Assistant), │
│   other Internet equipment and Website equipment, code, satellite.) │
└─────────────────────────────────────────────────────────────────────┘
                                   ▼
┌─────────────────────────────────────────────────────────────────────┐
│                    Short Welcome Message, then:                     │
│ Select Option 1 to report a found animal, Option 2 if you are a vet, or Option 3 if you are an animal control │
│                              officer.                               │
└─────────────────────────────────────────────────────────────────────┘
```

| Option 1 | Option 2 | Option 3 |
|---|---|---|
| ▼ | ▼ | ▼ |
| see FIG. 4a | see FIG. 4b | Please input code for missing animal.  400 |

Caller inputs code.
System asks for confirmation.
If wrong, repeats process.   — No Yes
▼
System checks to see if that animal has been reported missing.
If wrong, repeats process.   410  → DB process M Yes
▼
Thank you.
The animal is protected and covered by the Registry.
You will be paid your standard fees for emergency medical care and boarding until the owner can arrange for pick up.

▼
System has caller input phone # (with error checking) and name.   420  → DB process N ▼
The owner will contact you about retrieval.
Enter your Fax # for complete billing and contact info. (with error checking).   450  → DB process O ▼
Thank you and goodbye.   460

Fig. 4c

These database processes are detailed steps that expand on selected Fig. 4a, 4b and 4c flowchart boxes.

Database Process G
1. Search animal database to be sure number is real.
2. Search Incident database to see if animal was reported missing.
3. If no incident record exists, create one.

Database Process H
1. Input info into Incident database.

Database Process I
1. Notify animal owner animal has been found.
2. If no medical care is necessary, give owner the finder's phone number and name, plus zip.
3. If medical care is necessary, let owner also know that the animal will be taken to a vet.

Database Process J
1. Search animal database to be sure number is real.
2. Search Incident database to see if animal was reported missing.
3. If no incident record exists, create one.

Database Process K
1. Input info into Incident database.
2. Notify animal owner animal has been found.
3. Let owner know vet phone number, name, etc.

Database Process L
1. Input fax into incident database.
2. Fax complete billing info to vet.

Database Process M
1. Search animal database to be sure number is real.
2. Search Incident database to see if animal was reported missing.
3. If no incident record exists, create one.

Database Process N
1. Input info into Incident database.
2. Notify animal owner animal has been found.
3. Let owner know animal services organization phone number, name, etc.

Database Process O
1. Input fax into incident database.
2. Fax complete billing info to animal services facility.

Fig. 4d

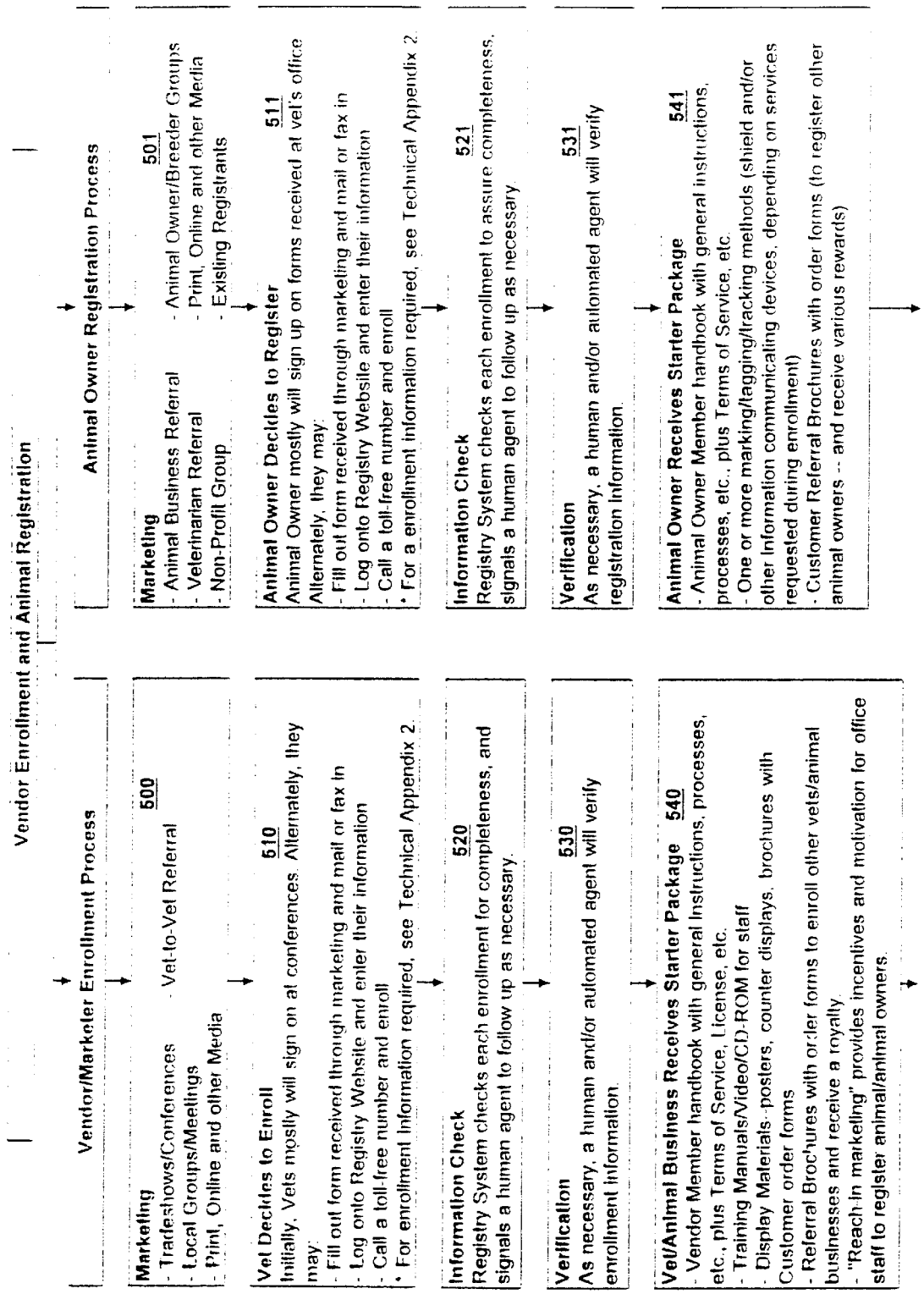

ANIMAL CARE REGISTRY SYSTEM AND METHOD

BACKGROUND OF THE INVENTION

1. Field of the Invention

The present invention relates to a system and method for providing a Registry System based on portable information borne by an animal for the animal's location and emergency information, reception/holding/treatment and payment authorization, the Registry System being accessible by at least one Communication Method which term ("Communication Method" or "Communication Methods") as used herein means telephone, wireless device, Website/Internet, broadcast television, cable television, fiber optic equipment, computer, pager, facsimile, cell phone, two-way radio, FM radio, AM radio, short wave radio, microwave device, U.S. Postal Service, private postal service, private delivery service, private messenger, e-mail equipment, PDA (Personal Digital/Data Assistant), telephony (the term "telephony" is defined to mean herein means for communicating using voice, telephone equipment, and computers together), other Internet equipment, Website equipment, code, and satellite. Provision is made for rewarding users of the Registry System.

2. Description of Related Art

There are some 100,000,000 dogs and cats in the United States and there are some 28,000 veterinary practices. Almost all animal owners fear losing their animals, especially animal companions, either to an accident or to an animal shelter. All animals can stray away, become lost, possibly injured, throughout their lifetimes. More than 80 percent of missing and lost cats and dogs never return. Most taken to shelters are euthanazed.

There exist many approaches to identifying animals: photographs, branding, tattooing, noseprints, tags, and bodily insertions. There is at least one existing system and one published patent application for locating the owners of animals and providing veterinary, medication, health history, and other information that is supported by a database of animal-related information and is both telephone and Internet accessible, see the world wide web at mypetid.ca and U.S. Patent Application 2002/0116390, published Aug. 22, 2002, both of which are hereby incorporated by reference as if fully set forth herein. MyPetID is an existing system that focuses on pet identification and providing pet information. MyPetID only provides a receiving/holding/treating veterinarian with information as to whether or not a found pet has insurance. MyPetId does not provide a receiving/holding/treating veterinarian with authorization to receive/hold/treat a pet and authorization for payment for this reception/holding/treatment by any payment method. The system and method of the recently published U.S. Patent Application No. 2002/0116390, differs from the present invention in that the referenced application focuses on pet shops as the point of entry into a pet identification service whereas the present invention is centered on veterinarians as the point of entry into the system. The system and method of the recently published U.S. Patent Application No. 2002/0116390 also lacks, among other things, authorization for reception/holding/treatment by a veterinarian and a method for, and authorization of, payment for reception/holding/treatment. Finally, unlike any available or published pet location system, the system and method of the present invention can offer a reward as an incentive to animal finders to use the Registry System to obtain reception/holding/treatment from any veterinarian for a found animal and can provide information concerning a found animal to the animal's owner.

SUMMARY OF THE INVENTION

In the discussions of the present invention which follow it is to be understood that the term animal is used for illustrative purposes only and comprises any animal that can bear an identification unit comprising an identification code comprising letters and/or numbers and/or symbols, wherein animal comprises companion animals, breeding stock, show animals, work animals, racing stock, livestock, and guard animals.

Thus, there is a need for an animal location system (with rewards to provide incentives to those who find and report missing animals) that identifies animals as to their owners and may provide medical histories, authorizes a veterinarian to stabilize/treat an injured animal, and provides a pre-approved payment method, up to an initial threshold amount.

The present invention is a system and method for attracting and keeping animal care provider and animal owner clienteles, providing and accessing an information Registry System for servicing these clienteles with regard to recovery and reception, holding, and/or treatment of missing, lost, stolen and injured animals by veterinarians or other professional animal caregivers, and an Information Unit or Shield carried by the animal that identifies the animal for obtaining Registry System services.

The system and method of the present invention incorporates a business model based on professional gatherings, veterinarians, individual and business animal care providers, animal boarding facilities, print, Internet, and broadcast media as credible sources for a registration brochure and (with respect to veterinarians and animal care providers) as recipients of a fee for each registrant. The business model comprises veterinarian-to-veterinarian recommendations and provides already enrolled veterinarians to answer questions potential veterinarian participants may have. The present invention is centered on veterinarians as the point of entry into the system. A similar reliance is placed on individual and business animal care providers, and animal boarding facility interactions as well as owners of registered animals to owners of non-registered animals.

The data used to reunite an animal with its owner, provide veterinary reception/holding as well as emergency treatment to an injured animal, and provide information to an owner about the location and conditions of a lost/missing animal, is organized by the present invention in a Registry System comprising one or more databases. Access to the Registry System of the present invention comprises inward toll and toll free telephone numbers and the Communication Methods.

In a preferred embodiment of the Registry System, the system and method of the present invention provides at least one database comprising animal emergency contact information, reception/holding/treatment and payment authorization information, and incident recording and tracking information. Corresponding portable information (letters and/or numbers and/or symbols) is contained in an Information Unit or Shield borne by an animal in any of several ways, comprising: being worn as a tag, tattooed or branded on the skin, attached to the animal, inserted into, or under, the skin of the animal, or otherwise borne by a registered animal. The portable information comprises a unique animal identification code which comprises a plurality of numbers and letters and single character typographic symbols for uniquely identifying the database records for the animal bearing the portable information. Using this unique animal identifier, emergency services can be provided (such as treatment by a veterinary health care provider and payment for reception/holding/treatment to a veterinary health care provider) while the animal's owner is located and informed of the animal's location and condition.

The Information Unit or Shield borne by the animal enables identification of the animal's corresponding database records via automation or human operator so that location, return, reception/holding/treatment, and payment for reception/holding/treatment may be accomplished, and, when authorized, payment of a reward to the caring person that delivered the animal to any close, convenient veterinarian, or otherwise provided animal location and status information to the Registry System. An ideal arrangement includes a small tattoo mark on a registered animal's ear (which tattoo provides notice of an identification chip implanted in the animal) plus a shield on a bridle, collar, or other external carrying device. Finally, unlike any available or published pet location system, the system and method of the present invention can offer a reward as an incentive to animal finders to use the Registry System to obtain reception/holding/treatment from any veterinarian for a found animal and provide information concerning a found animal to the animal's owner.

BRIEF DESCRIPTION OF THE DRAWINGS

FIGS. 2a–c illustrate the business process logic flow of a preferred embodiment of the present invention.

FIGS. 3a–d illustrate a preferred embodiment of a member registration contact tree system and associated database interactions, respectively.

FIGS. 4a–d illustrate a preferred embodiment of a non-member registration contact tree system and associated database interactions, respectively.

FIGS. 5a–b illustrate a preferred embodiment of the enrollment and registration function of the present invention.

DETAILED DESCRIPTION OF THE INVENTION

Figure 1:
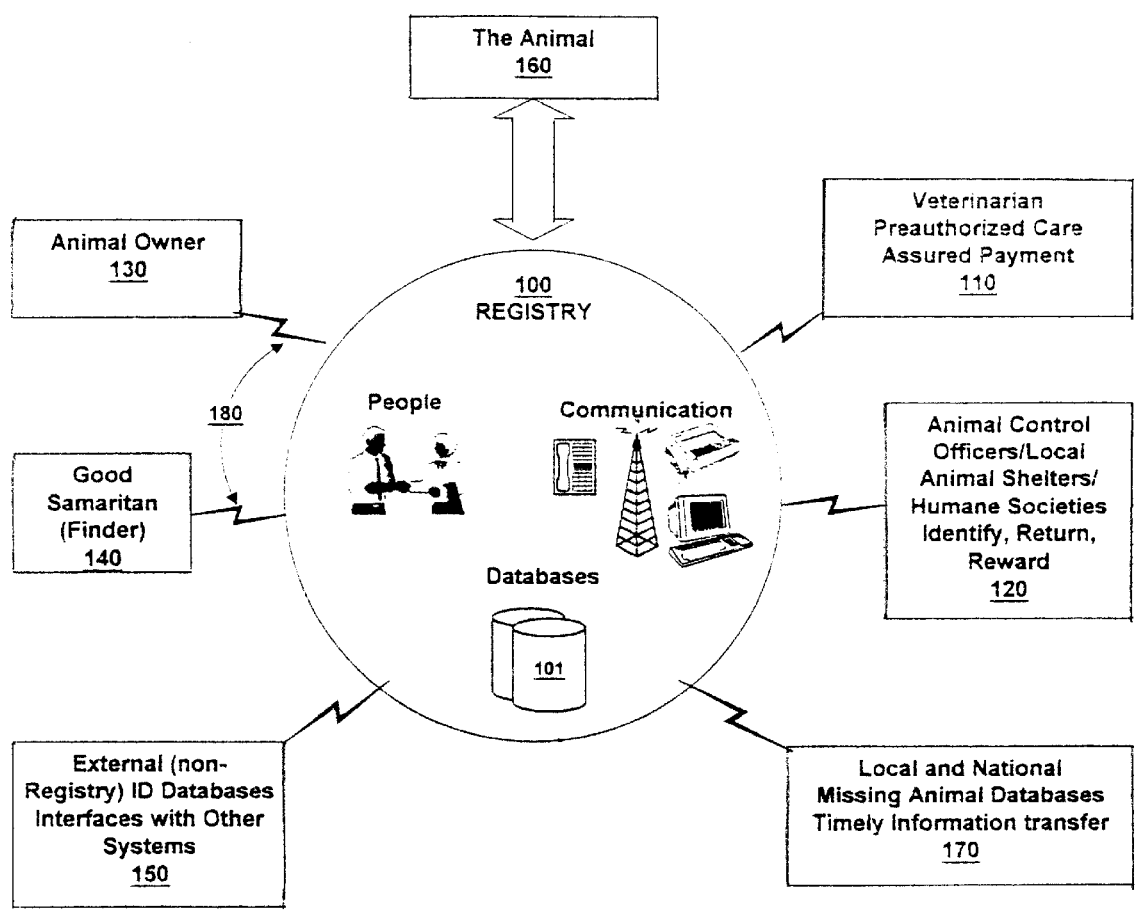
FIG. 1 illustrates an overview of the Registry System and its interfaces with individuals, organizations and other systems using an inward toll free telephone number and the Internet.

FIG. 1 provides an overview of a preferred embodiment of the interfaces of the system and method of the present invention. The Registry System 100, comprises at least one database 101 and the Registry System is accessed using the Communication Methods 180, by Veterinarians 110, Animal Shelters 120, Animal Owners 130, Good Samaritans 140, and External Animal Location Systems 150. Interfaces to the Registry System are also provided for the Animal (using the Information Unit or Shield borne by the animal) 160 and for information transfer to and from other databases 170. The Communication Methods connect each of elements 110, 120, 130, 140, 150, and 170 of FIG. 1 to the Registry System 100.

Figure 9:
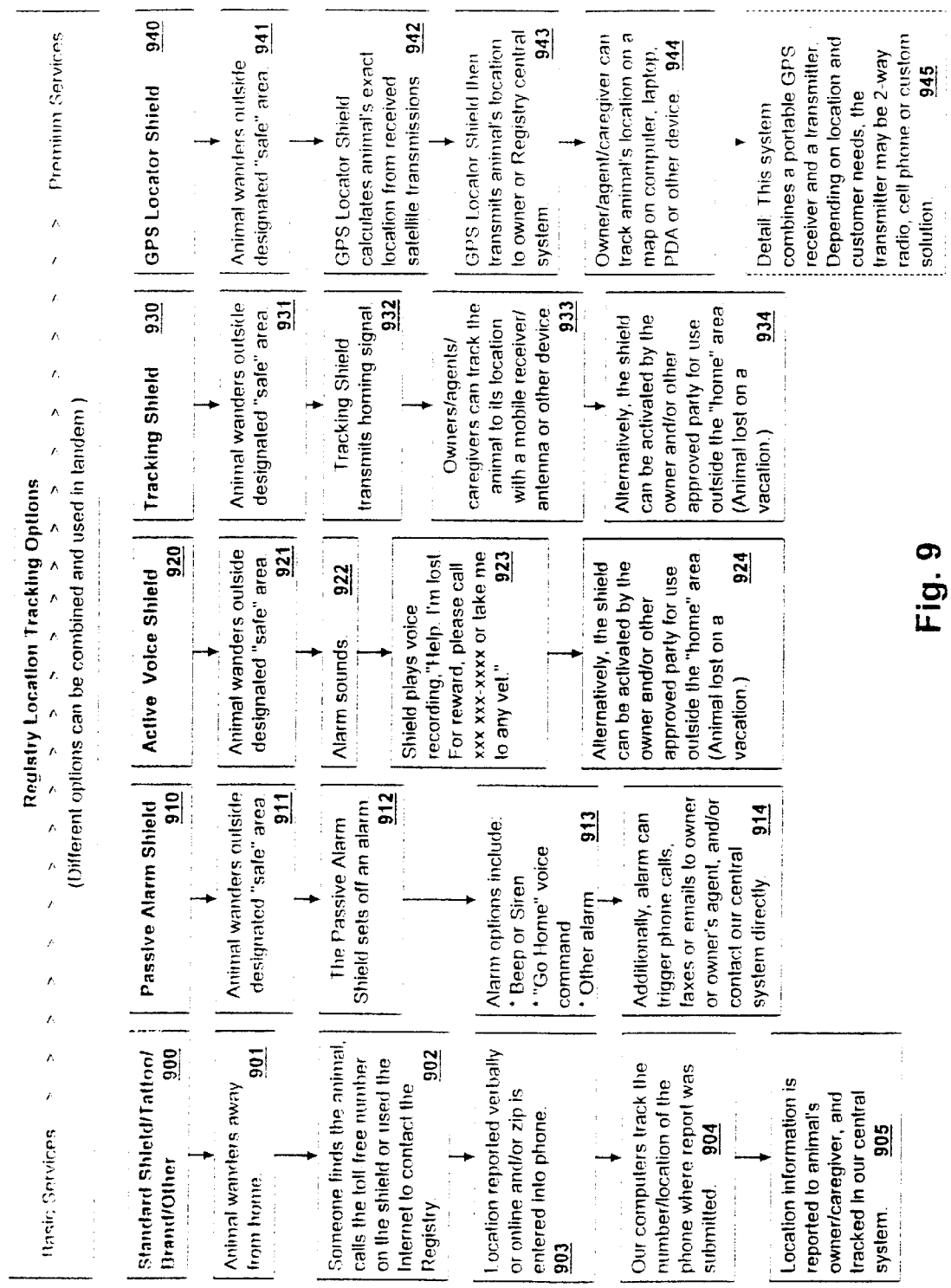
FIG. 9 illustrates preferred embodiments of location tracking options of an Information Unit or Shield.

In an alternative embodiment, the Information Unit or Shield can be any one of several types, as illustrated in FIG. 9, allowing an animal to be identified by a finder 900 or through active on-animal signaling 910, 920, 930, and 940. In the case of a Global Positioning System (GPS) capable Information Unit or Locator Shield 940, the animal is actively tracked using the GPS so the unit can be located automatically, without the input of a finder/veterinarian/owner to the Registry System. Registry-designated personnel will rescue a GPS located animal according to instructions provided to the Registry by the registered animal's owner.

The contents of the various databases are discussed in Section B below which is titled "Registry."

A. Business Process

Figure 2A:
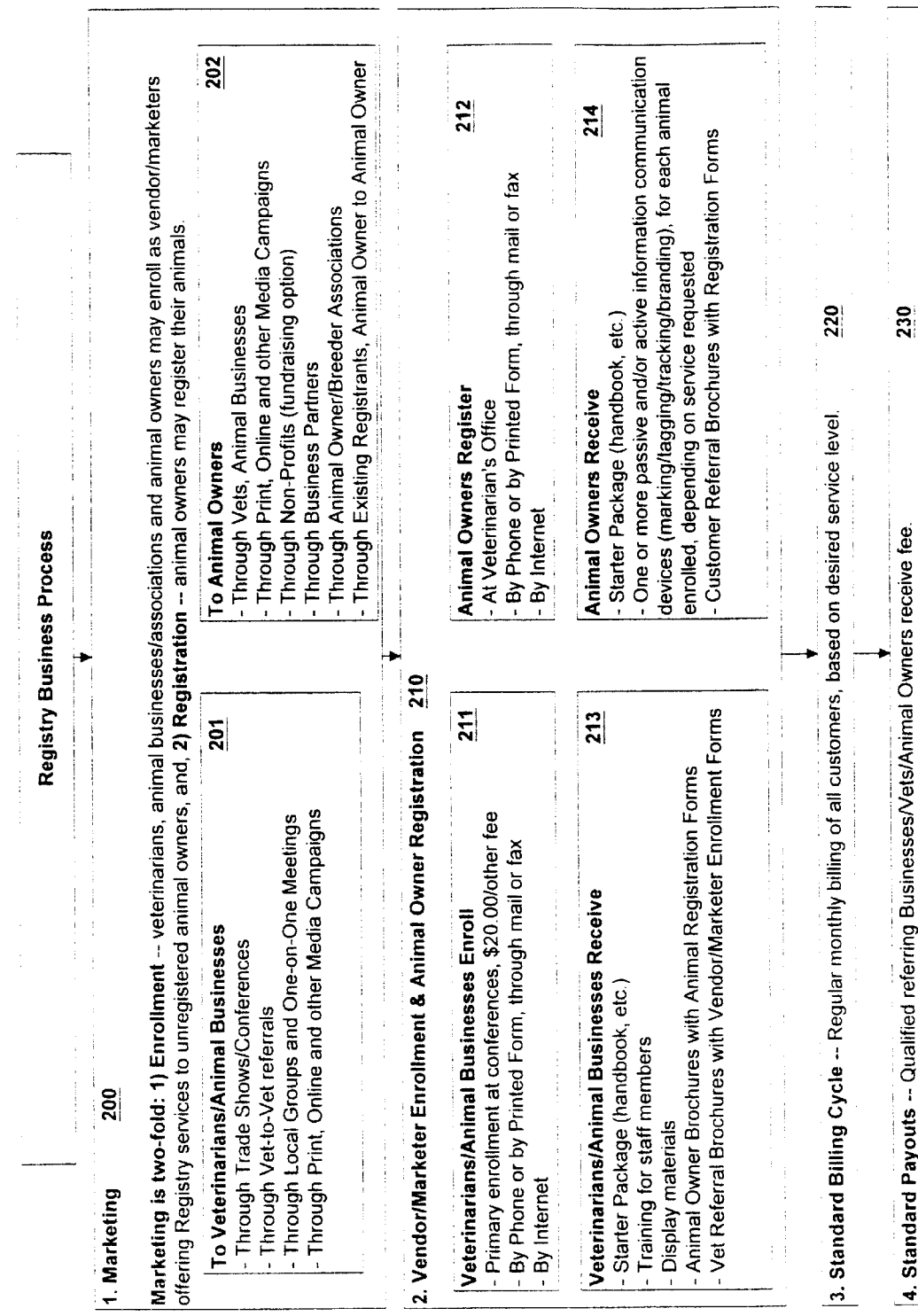

FIGS. 2a–c illustrate a preferred embodiment of the logic flow of the business process of the present invention, which comprises marketing 200, enrollment/sign-on 210, billing 220, payouts 230, continuing contact and support 240 and marketing 280, incident processing and tracking 250, and special billing 260 and special payouts 270.

In one embodiment, the Registry System uses pooled risk (i.e., insurance) to provide for any needed payment by the Registry System. In this embodiment, the registered animal owners (discussed below) will make periodic or aperiodic premium payments and these funds (including amounts earned by investing these funds) will be used to make the payments discussed below (as for example to veterinarians, animal caregivers, and others).

A.1 Marketing 200

In a preferred embodiment, marketing is two-fold: (1) to veterinarians and animal businesses to become vendors 201 and (2) to animal owners 202 to register their animals through professional veterinarians and animal businesses, comprising, e.g., grooming facilities, animal stores, and boarding facilities 201. Veterinarians are solicited to become vendor/marketers through trade shows/conferences, referrals, presentations to local veterinarian group meetings and one-on-one meetings. Other marketing techniques comprise print, online, telephone, optical, and media campaigns and may use the Communication Methods.

Non-registered animal owners are also solicited through veterinarian vendor/marketers and animal business vendor/marketers, print, online, telephone, and media campaigns, non-profit organizations, business partners, owner associations and referrals from registered animal owners to non-registered animal owners. These marketing techniques used to reach non-registered animal owners may use the Communication Methods. All persons/entities involved with the Registry System of the present invention may optionally receive various types and levels of compensation.

Thus, in a preferred embodiment, the system and method of the present invention is based on the enrollment of veterinarian vendor/marketers and animal business vendor/marketers and registered animal owner vendor/marketers who then agree to communicate the system and method of the present invention to their clientele and associates. A display with brochures in the veterinary doctor's and animal business facility's premises is one means employed as an animal registration attraction; another is a brochure attached to receipts and bills provided by the veterinary doctor and animal business to clients as potential registrants, each having the originating veterinarian or animal business clearly identified. In a preferred embodiment, registrations are forwarded by registrants directly to a central location (the Registry System), thus avoiding paperwork for the registering veterinarian and animal business. However, the veterinarian and animal business is kept fully informed of enrollments originated by them. Alternatively, the animal owners can be solicited directly by the Registry and/or by registered animal owners enrolled as vendor/marketers.

A.2 Enrollment and Registration 210

In a preferred embodiment, there are several types of enrolled vendor/marketers 210 comprising veterinarians, animal-oriented businesses, animal owners, animal insurers, animal professionals, animal control officers and their associates, animal breeding registries and associations, animal welfare/care associations and persons which may be tax-supported, non-profit, or for profit.

In a preferred embodiment, veterinarians and animal businesses enroll primarily at conferences; they can also enroll 211 by Communication Methods. Veterinarian and animal business vendor/marketers receive a starter package, training, display materials and brochures with registration forms for registering animal owners and other veterinarians and/or animal businesses 213.

In a preferred embodiment, animal owners register their animals via a registration brochure obtained at a veterinarian's office or an animal business facility 212. Alternatively, animal owners can register their animals enroll via Communication Methods. Animal owner registrants receive a starter package, Information Unit or Shield(s) to be borne by the animal(s), and customer referral brochures with registration forms for registering other animal owners and veterinarians and/or animal businesses 214.

It is not necessary for a veterinarian or animal care facility professional to be enrolled as a Registry System vendor/marketer in order to receive, hold, or treat a registered animal; any veterinarian or animal care facility professional may receive, hold, or treat a missing, straying, or lost registered animal.

The intent of this preferred embodiment of a marketing focus is credibility, i.e., that a lost or injured animal is received and cared for at any licensed veterinary or animal business, with the receiving or holding or treating facility taking authorized charge and the Registry System and method of the present invention providing a pre-authorized reward to the caring individual who took the animal to the most convenient care facility. When authorized, the reward is charged to the animal owner's credit card, deducted from the animal owner's debit card, automatically charged to the animal owner's account, or wire transferred from another account maintained by the animal owner.

For example, the Registry System tracks all incoming calls and calls an owner automatically when an incident concerning an enrolled animal is received, providing the owner with location, contact and other information collected by the incident report. Thereafter, the animal owner may intervene at any time.

In a preferred embodiment, veterinarians and animal businesses pay 211 a one-time, small enrollment fee (thereby becoming Registry System vendor/marketers) and receive fees 230 when the animal registrations that they originate reach a threshold. Thus, the registration process of the system and method of the present invention enhances the care dynamic between and among veterinarians and between veterinarians and their animal-owning clientele and provides a similar enhancement and incentive for animal businesses. In this embodiment, owners and their already trusted care providers are partners not only in caring for an animal but also in providing the Registry service for recovering and treating missing, straying, or lost and possibly injured animals.

A.3 Standard Billing Cycle 220

In a preferred embodiment, animal owners are billed 220 at regular, agreed upon intervals, typically monthly. Amounts billed reflect services provided during the immediately preceding interval, as well as a baseline charge for registration and maintenance of an animal's information by the Registry System. Registered animal owners may also pay the fees (for veterinary and animal care services) directly to the provider when the registered animal owner is reunited with the animal at the holding facility.

In this preferred embodiment, a plurality of animal health/condition and location monitoring services are disclosed in FIG. 8 below. In this preferred embodiment, a plurality of animal location and tracking services are disclosed in FIG. 9 below. Billing is for the appropriate service level plus any special charges.

A.3.1 Shield Service Levels

Shield service levels are disclosed below in connection with the discussion and explanation of FIG. 9.

A.3.2 Health/condition Monitoring Service Levels

Various health/condition monitoring service levels are disclosed below in connection with the discussion and explanation of FIG. 8.

A.4 Standard Payouts 230

In a preferred embodiment, fees 230 are provided to veterinarians, animal businesses and animal owners not only for registering animal owners, but also for providing referrals. The system and method of the present invention comprises a veterinarian-to-veterinarian introduction aspect designed to provide maximum program expansion in the veterinary community. Veterinarians in each state, for example, are also identified as points-of-contact for potential veterinarian enrollees to contact for a veterinarian-to-veterinarian heart-to-heart conversation for answers and dialogue when enrolling in or using the Registry System. A similar paradigm applies to the community of animal businesses, and registered animal owner to non-registered animal owner which may or may not involve fees.

A.5 Continuing Contact and Support 240

In a preferred embodiment, there is continuing contact and support provided by the Registry System 241 reaching out to veterinarians, animal businesses, and animal owners as well as their employees to offer training and marketing materials and to solicit feedback concerning the Registry System and associated services. Employees of the Registry System also send 242 newsletters to animal owners, make follow-up calls to animal owners, and perform advance marketing of new features to animal owners.

A.6. Incident Processing and Tracking 250

In a preferred embodiment, incident processing and tracking comprises the steps of processing missing animal reports 251, found animal reports by a third party 252 or a veterinarian 253, special care for extended missing periods 254, and concierge services 254.

a. Animal Owner Makes Missing or Lost Animal Report 251—When an animal owner or other responsible party contacts the Registry System, using the Communication Methods or otherwise, to report a registered animal as missing/lost, the report is entered into the Registry System databases and is automatically filed with any and all related lost animal databases with which the Registry System interacts. In this preferred embodiment, there is automatic notification of all regional animal shelters. The registered owner is informed of all facilities, organizations, and persons notified during the search for the owner's registered animal. If a reward is offered, the automatic notification comprises this information as well. An automatic call-back is made periodically to the animal owner to determine if the animal has been found or has returned. Further details about the operation of the contact system (whether by telephone, Internet, or the Communication Methods or other means) in connection with the Registry Databases are provided in, and in the discussion below with respect to, FIGS. 3a, 3b, 3c, 3d, 4a, 4b, 4c, 4d, 6a, 6b, 7a, and 7b.

b. Third Party Makes Missing Animal Report 252—When a finder obtains contact information from the Information Unit or Shield and reaches the Registry System by an inward toll free telephone number or the Internet or other provided means, the Registry System collects contact information, ascertains the animal's condition and asks the finder to wait a finite time for the owner to make contact and then the Registry System contacts the owner with the finder's contact information. The Registry System optionally provides up to the nearest five veterinarians (and animal care facilities, or combination thereof) to the finder's location along with driving instructions and times. If the finder cannot wait, the animal is injured, or the owner does not respond, then the finder is advised to take the animal to the most appropriate and convenient of the five facilities and the Registry System optionally automatically contacts the selected facility. The selected facility contacts the Registry System and is assured of payment and the owner is contacted with the animal's condition and location. The animal owner calls the selected facility and arranges pickup and payment for services provided. If the animal owner does not arrange to pay for care and pick up the animal, the Registry System takes over this responsibility and assures the selected facility of payment for their services. Such incidents are closed automatically with all interacting databases being notified that the animal has been found.

c. Third Party Drops Animal At A Veterinarian 253—When a third party delivers an animal to a veterinarian, the veterinarian contacts the Registry System to report an incident and is assured of payment and the owner is contacted with the animal's condition and location. If the animal owner does not arrange to pay for care and pick up the animal, the Registry System takes over this responsibility and assures the animal care facility of payment for their services. Such incidents are closed automatically with all interacting databases being notified that the animal has been found.

d. Special Care 254—When an animal is missing for an extended period, extra cost services are rendered on an as-requested basis. The Registry System automatically calls the animal owner on a regular basis to advise that the system is still seeking the animal. These services comprise animal ambulance, animal attendant, animal transport, animal detective services, animal ground, sea, and air search and rescue, special care referral, animal boarding and entertainment/recreation, monitoring while stationery or in transport, activities to curb and convict those undertaking unlawful acts against registered animals.

e. Concierge Services 255—Concierge services are extra cost services which are provided on an as-requested basis and comprise, but are not limited to, counseling for emotional stress, assistance in launching a missing animal campaign, Registry System arranging pick-up of found animal, tracking and notification when animal leaves designated area, tracking of lost animal via satellite system, vital sign monitoring, private investigation services, and bonded or unbonded rewards for information leading to the arrest and conviction of perpetrators of crimes against registered animals. Concierge services may also include counselors to help with the emotional loss of losing an animal, animal's vital sign determination and transmission to designated recipient, animal private investigation, bond to counter unlawful actions against registered animal, reward for recovery of animal, transport of animal, attendant for animal, entertainment of animal, relaxation of animal, exercise of animal, search and rescue for animal, and communication to the animal or to the animal owner of notices designated as noteworthy by the registry system such as birthday greetings, holiday cards, holiday postcards, appointments, reminders for vaccinations, examinations, and other periodic and aperiodic occurrences.

Inward toll-free 800 number type telephone communications and bill-to-caller 900 number type telephone communications are also used by the Registry System. When launching a missing animal campaign, in addition to notifying local print, broadcast, and cable media outlets, the Registry will arrange for posters (with or without a picture of the missing animal), postcards (with or without a picture of the missing animal), and door hangers (with or without a picture of the missing animal) all of which can either be printed on the registered animal owner's own computer printer or prepared by the Registry and delivered to the registered animal owner for distribution by the owner and the Registry.

Concierge services may optionally include a small card suitable for carrying in a wallet or purse or a card suitable for posting as a notice in a home or office which card instructs emergency personnel who find the registered owner disabled or absent to contact the Registry System using the Communication Methods and, for example, specified contact telephone numbers or Universal Resource Locators or e-mail addresses or other means to arrange care for the registered owner's animals during the owner's period of disability or unavailability. The registered owner will be able to authorize the Registry System to obtain and pay for a locksmith, for example, to gain access to the owner's animals and for a veterinarian or other animal care giver to transport, hold, and care for the animal during the owner's disability or unavailability. The card will also advise whether the owner has chosen to have the Registry System provide notice of the owner's disability or unavailability to emergency response organizations such as the local police, fire, and private security alarm organizations.

Emergency monitoring and alarm organizations (such as those who notify public authorities in case of fire, intrusion, or other emergency) may have links to the Registry System. When the Registry System receives notification of an emergency involving, for example, a fire at the home of a registered owner, the Registry System, as a concierge service, will notify the designated veterinarian or animal caregiver who, by pre-arrangement, is authorized to enter the home, find the animal, and care for and provide services to the animal in the owner's absence or disability. Through the Registry System, the veterinarian or animal caregiver is assured of payment for services rendered and expenses incurred.

A.7 Special Billing 260

In a preferred embodiment, any services above and beyond the agreed monthly charge for the Registry System is specially billed. These special services comprise pre-authorized rewards, medical and boarding services, and veterinarian reception/holding of an animal from a third party. Special billings are charged to an animal owner's pre-authorized credit card 260 deducted from a pre-authorized debit card, deducted from the registered animal owner's Registry System account, charged to the registered animal owner's Registry System account or wire transferred from a bank account of the registered animal owner. In another embodiment the Registry System involves pooled risk (insurance) as a payment means for special billing.

A.8 Special Payouts 270

In a preferred embodiment, special payouts are made by the Registry System billing an animal owner's preauthorized credit card as payment for special services included in special billing 270.

A.9 Continued Marketing 280

In a preferred embodiment, the Registry System uses success stories and testimonials from satisfied animal owners to maintain and increase the registered base of animal owners, veterinarians, and animal businesses 280. Other animal related and non-animal related products and services may optionally be marketed using the Communication Methods or other means to individuals and organizations included in the Registry System database.

B. Registry 100

The Registry System and Registry Databases are illustrated in FIG. 1. In a preferred embodiment, the Registry System comprises information stored in databases as well as services for accessing and updating the databases so that animals are registered, owners and veterinarians, are enrolled, animal lost/found incidents are reported and closed out, and accounting is handled for payments and receipts.

B.1 Registry Databases 101

B. 1.1 Owner Database

This database is the main repository of animal owner information. Each owner is uniquely identified by owner number, letters, and/or symbols. Owner information comprises contact information (primary and alternate), credit card information for billing, debit card information for payment, owner bank account information for wire transfer bill and receipt of payment, and owner account information for payment. All databases contain open fields and additional options for additional information and functions. Repeating groups are provided for fields that may repeat, such as contact phone numbers. A back-up payment source of each type may also be provided. The owner database comprises the following fields:

owner number;

owner name;

billing address;

repeating group for authorized hierarchy of payments by payment type, e.g., credit cards, debit cards, Registry account, bank account;

mailing address for membership materials;

referring veterinarian, boarding facility or other animal care business or professional or a registered owner enrolled as a vendor/marketer;

veterinarian-to-veterinarian referral;

in-house Representative (for additional incentive payment);

outside Representative;

start date;

financial hold (non-payment; also relates to payment of referring Veterinarians);

Phone No. 1—for general contact about setup and services;

Phone No. 2—repeating group for contact when animal reported found;

Facsimile No.—repeating group for contact when animal reported found;

e-Mail Address—repeating group for contact when animal reported found; and

Animal identification code—repeating group of uniquely identified animals using numbers and/or letters and/or single character typographic symbols.

B. 1.2 Animals—All animals are uniquely identified by an identification code comprising numbers and/or letters and/or symbols), in a preferred embodiment. Associated with each identification code is both animal and owner information. Animal information is a complete description of the animal comprising the following items which represent physical characteristics (and may include an image of the animal), the medical history of the animal, and authorization for a licensed veterinarian to provide emergency health care services:

owner number;

animal identification code;

name;

species;

breed;

age;

sex;

type;

color;

other identifying information;

home address;

reward;

image;

call name of animal;

repeating group for type and other data of each Information Unit or Shield borne by the animal;

repeating group for medical history with fields for disease, medication, dosage, and related information repeating group of veterinarian name, address, specialty, authorization to treat, initial amount charged threshold, and related information;

B. 1.3 Open Incident

This database records all incidents reported to the Registry System. A repeating group contains finder information and identifies finders by type. For example, a first finder is the individual who calls in to report that they found an animal. The remaining finder records track the individual(s) and organization(s) through which the animal passed. The open incidents database comprises the following items:

incident No.;

animal code;

owner No.;

status;

date/time stamp when reported lost;

name of incident reporter;

location where lost comprising street address, state, county, city, intersection and/or zip code; and repeating group of finder information: owner flag, name, address, phone No., date/time stamp for each contact from a finder relating to a specific lost animal incident number.

B. 1.4 Vendors —information about vendors comprises the following items:

vendor identification code;

type (veterinarian, boarding facility, animal shelter, animal control, internal representative, owners of registered animals designated as vendors/marketers to non-registered animal owners);

name;
address;
e-mail;
facsimile number;
contact;
contact address;
contact e-mail;
contact facsimile number;
organization name;
business address;
billing address; and
other 1099 information.

B.1.5 Accounting Records

This database contains aged accounts payable and receivable records and comprises at least:
account code;
account type;
vendor identification code; and
other necessary information.

B.2 Registry System Services

In a preferred embodiment, the services for accessing and updating the Registry Databases are either a human operator and/or an interactive telephone voice response system for member/non-member call-in of incidents, or a comparable World Wide Web browser application for interactive reporting of incidents. In any case, the data gathered and the system checks performed are the same. While the discussion is in terms of a contact via a telephone system, the flow chart and database processes are essentially the same if the contact is via any of the Communication Methods.

The Registry System can be operated on a variety of standard readily available hardware and software. The system will operate on a Dell PowerEdge server model 4600 or 6600. Additional computers (connected via a network to the server) for data input and general business use can be Dell Precision Workstation Model 350. The telecommunications hardware is an Intel Dialogic Model D/41ESC analog telephony card which can handle four (4) telephone lines. If more telephone lines are desired, additional Intel Dialogic Model D/41ESC analog telephony cards can be added to the system. The server operating system can be Microsoft 2000 Server. The operating system for the computers attached to the server via a network is Microsoft Windows XP. The telecommunications software can be Voice XML Version 2.0 which is open source standard software available, for example, from Maywehelp.com of Phoenix, Ariz.

B.2.1 Communication Tree

A plurality of communication trees or other Communication Methods (which may also be referred to as telephone response systems or response protocols) are provided in a preferred embodiment, for interfacing with users of the Registry System, comprising the following communication trees.

Figure 3A:
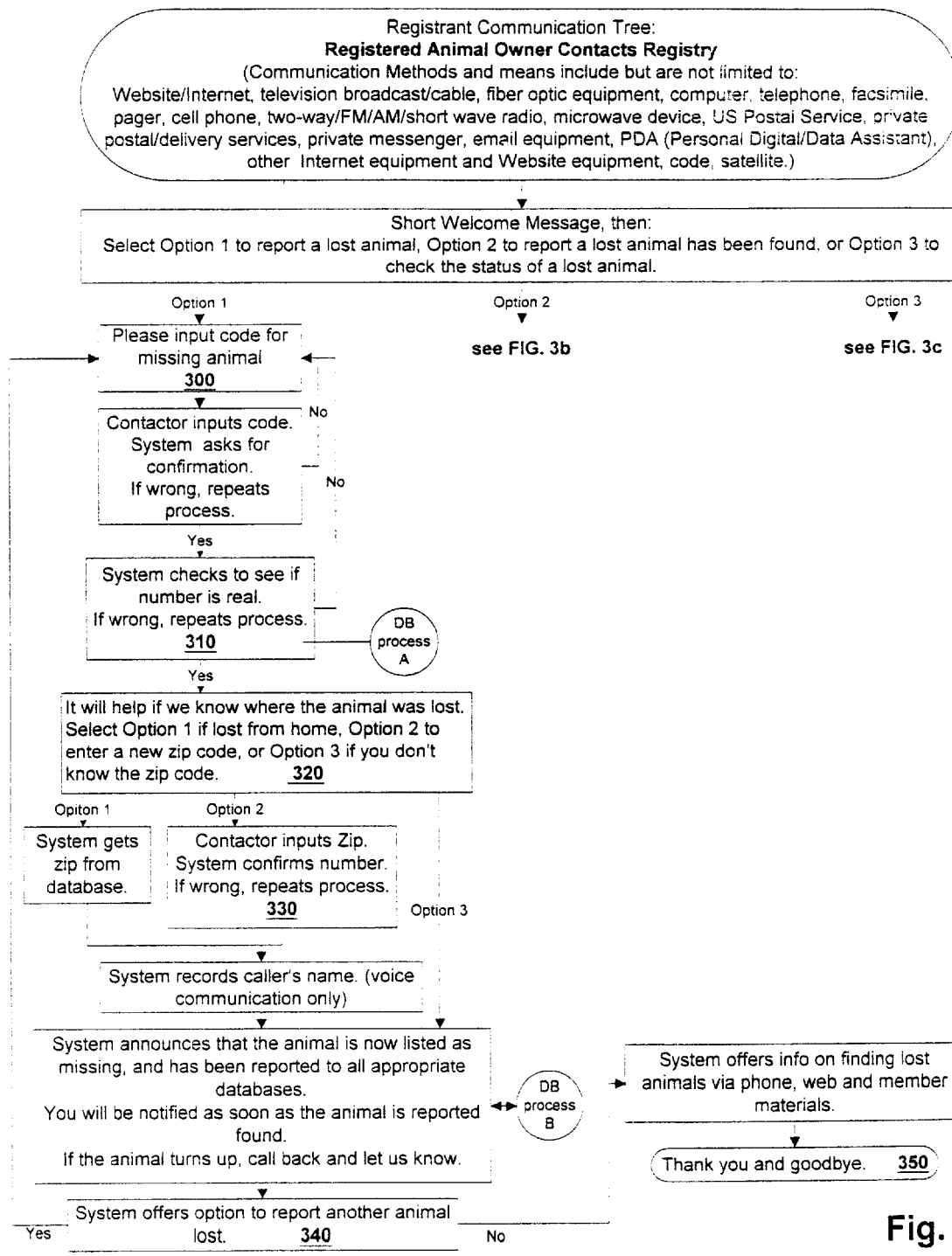
Figure 3B:
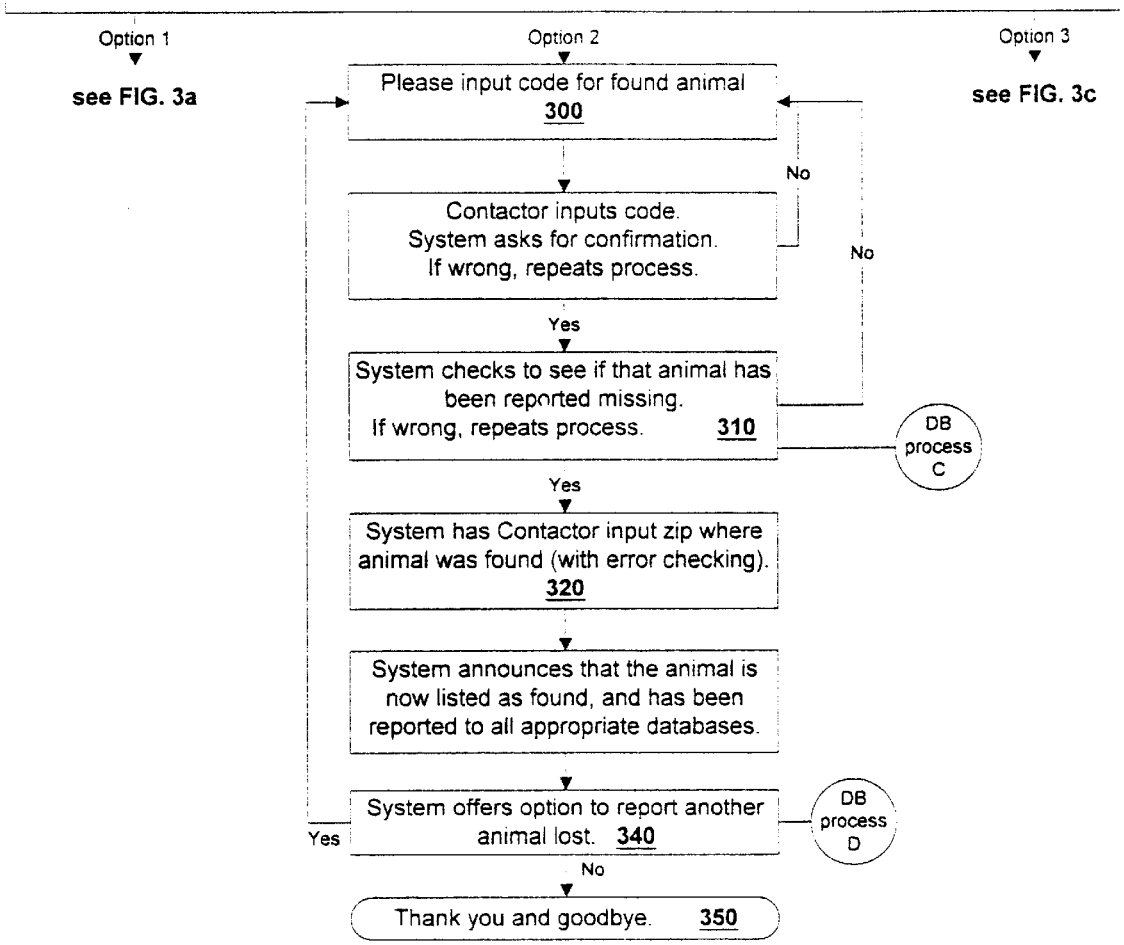

B.2.1.1 Member Call-in—FIGS. 3a, 3b, 3c, and 3d illustrate a preferred embodiment of a flowchart of telephone interaction or other Communication Methods and database processes for a contact by a Registry System member with the Registry System to exercise one or more of three System options which options are: 1—to report a missing animal; 2—to report a found animal, and 3—to obtain the status of a missing animal, to review and update information stored in the Registry Databases with respect to an enrolled animal. FIGS. 3a, 3b, and 3c set forth the response protocol and show the relationship of the responses to the database processes. FIG. 3d sets forth the related database processes.

For each option, the caller inputs an identification code 300 that the Registry System checks for validity 310 and if valid the Registry System then processes the type of input. For a missing animal report the Registry System solicits where the loss occurred 320 and enters the loss into an incident database, asking for confirmation 330 of the information provided by the caller. A similar process is followed for a found animal being reported by a caller 310–320. In the case of a status request with respect to a missing animal, the Registry System provides 330 the current status from a database. In each case the Registry System asks the caller if another request is desired 340 and repeats the process if the response is yes or terminates the call if the response is no 350.

Throughout the operation of the member phone system, the system and method of the present invention accesses Registry Databases and makes appropriate entries in Registry Databases as indicated in database processes A, B, C, D, E, and F of FIG. 3d.

FIG. 3d illustrates the database processes associated with the activities of the registrant contact tree of FIGS. 3a, 3b, and 3c.

Database processes A and B are performed in response to the report of a lost animal by a Registry System member. When a member inputs an animal identification code, the database process A searches the animal database to determine if the number is valid and database process A further determines if the incident has already been logged. Database process A provides to the caller a status report if the incident has already been reported which status report comprises information about when, by whom, and where the incident was reported.

If the there is no existing incident report then an incident report is created by database process B. The incident report comprises information concerning the date, time, animal identification code, caller's name, and the caller's zip code. Further, a link is created between the incident report and the appropriate animal owner data already stored in the Registry Databases.

Database processes C and D are performed in response to a report concerning a found animal. When a found animal is reported, database process C ascertains that the animal identification code entered is a valid code corresponding to a registered animal. Database process D enters the finder's data into the appropriate existing incident record, which is then marked closed. All appropriate interconnecting databases are notified that the incident is closed.

Database processes E and F are performed in response to a report to a Registry System member concerning a still missing animal. When a status check is made by a member concerning a prior incident report, database process E validates the animal identification code and database process F determines the appropriate status information to provide to the Registry System member calling for information concerning the missing animal.

B.2.1.2 Non-Member Call-in—FIGS. 4a, 4b, 4c, and 4d illustrate a preferred embodiment of a flowchart of telephone interaction or other Communications Methods and database processes for a contact by a non-registrant of the Registry System with the Registry System to exercise one or more of three System options for non-registrants. A non-registrant can only be calling to report a found animal so the system asks for the type of caller which types are: 1—an individual, 2—a veterinarian or an animal business owner, and 3—an animal control officer.

Figure 4A:
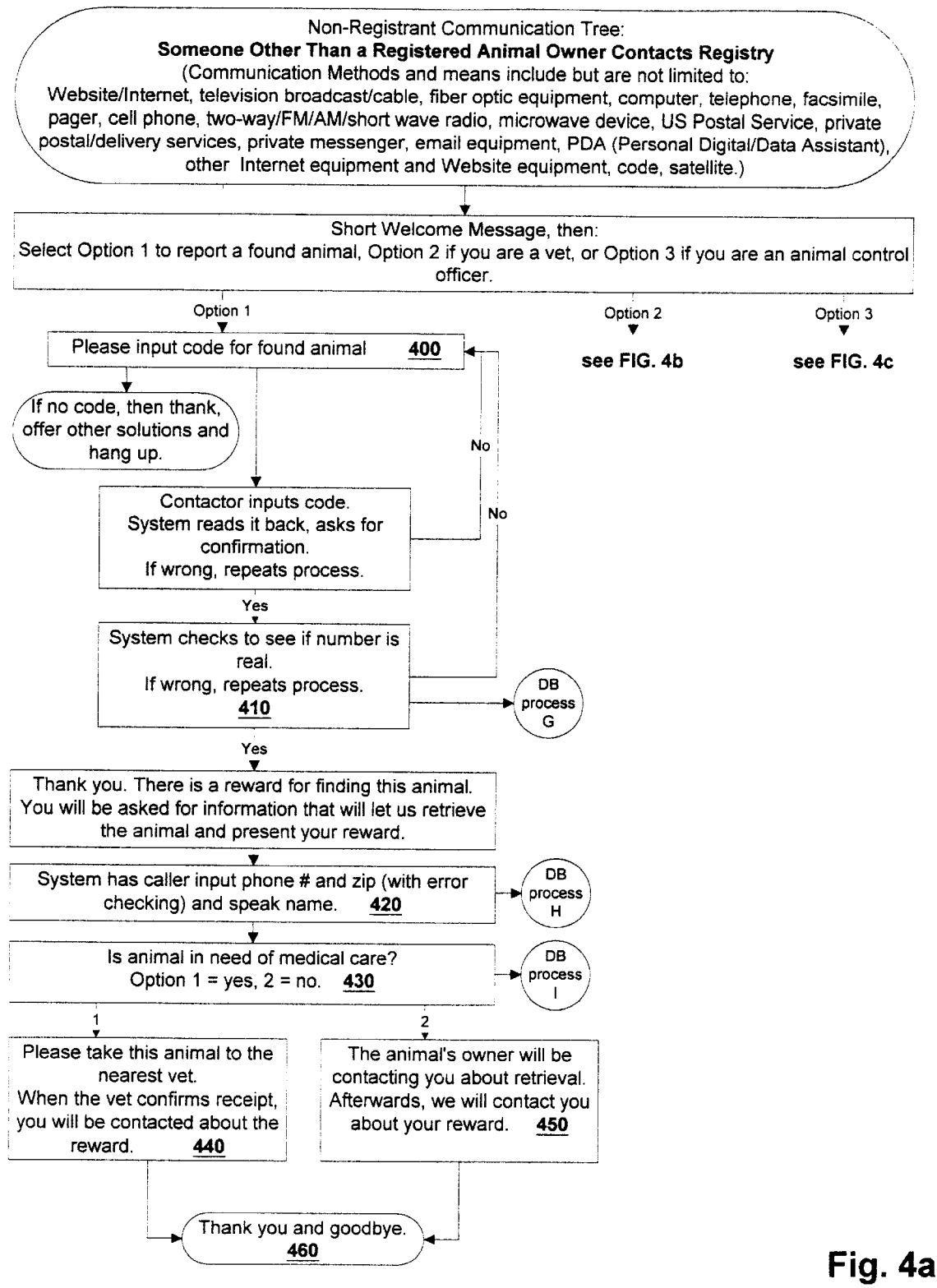

FIGS. 4a, 4b, and 4c set forth the response protocol and show the relationship of the responses to the database processes.

FIG. 4d illustrates typical database processes associated with the activities of the non-registrant contact tree of FIGS. 4a, 4b, and 4c.

For each option, the caller inputs an animal identification code 400 that the Registry System solicits and checks for validity 410. After confirming that a valid animal identification code has been received, the system advises an individual caller about the availability of an award 411 and solicits 420 further information about the whereabouts of the animal and the caller's telephone number. The Registry System records and optionally communicates all telephone numbers involved. If the caller is an individual, the Registry System inquires 430 as to whether the animal needs medical care and directs the individual to take the animal to a veterinarian 440. If there is a reward and the caller is an individual (including but not limited to an animal control officer), the Registry System informs the caller that he will be contacted about the reward 440. If the caller is a veterinarian or affiliated with an animal care business, the Registry System advises 412 or 413 that the provider's standard fees are paid for medical care and/or boarding, reception, or holding until the owner can arrange to retrieve the animal. If the caller is a veterinarian, affiliated with an animal care business, or an animal control officer, the system solicits 420 further information about the whereabouts of the animal and the caller's telephone number; the Registry System informs the caller that the animal owner will contact the caller about retrieving the animal 450.

The Registry System then terminates the call 460.

Throughout the operation of the non-member communication system, the system and method of the present invention accesses Registry Databases and makes appropriate entries in Registry Databases as indicated in database processes G, H, I, J, K, L, M, N, and O of FIG. 4d.

Database processes G, H, and I are performed in response to a contact by a non-member individual. Database process G searches the animal database to determine whether an identification code provided by a non-member is a valid animal identification code. If the number is a valid animal identification code, database process G determines if an incident with respect to the animal identified by the animal identification code has already been reported and logged into the Registry System. A status report is provided to the caller if the incident has already been reported which report comprises information concerning when, by whom, and where the incident was reported.

If there is no existing incident report then one is created by the database process G comprising date, time, animal code, caller's name and zip code and/or other identifying or locating information.

Database process H enters a new incident report into the Incident Database.

Database process I solicits the condition of the animal, instructs the finder to take an injured animal to the nearest veterinary care facility, informs the finder of the reward, asks for finder's address and telephone number or other identifying information (comprising the finder's social security number and/or driver's license number and/or telephone number(s)), reads the finder's phone number(s), and optionally reports this identifying information to the animal's owner.

Database processes J, K, and L are performed in response to a contact by a non-member veterinarian or animal service provider. Database process J validates the animal identification code provided by an animal service provider, searches for an existing incident report, and, if there is no existing incident report, creates an incident report.

Database process K collects caller information and stores it in the Incident Database.

Database process K also notifies the animal owner that the animal has been found and provides the contact information for the animal service provider that has found a registered animal.

Database process L collects billing information, such as the animal service provider's facsimile number, stores this information in the Incident Database, and provides complete billing information to the finding animal service provider.

Database processes M, N, and O are performed in response to a contact by a non-member animal control officer. Database process M validates the animal identification code that is provided by an animal control officer, searches for an existing incident report, and, if there is no existing incident report, creates an incident report.

Database process N collects caller information and stores it in the Incident Database. Database process N also notifies the animal owner that the animal has been found and provides the animal owner with the contact information for the animal control facility that has found a registered animal.

Database process O collects billing information, such as the animal control facility's facsimile number, stores this information in the Incident Database, and provides complete information to the animal control facility which has reported a found animal.

B.3 Enrollment/Registration

Figure 5B:
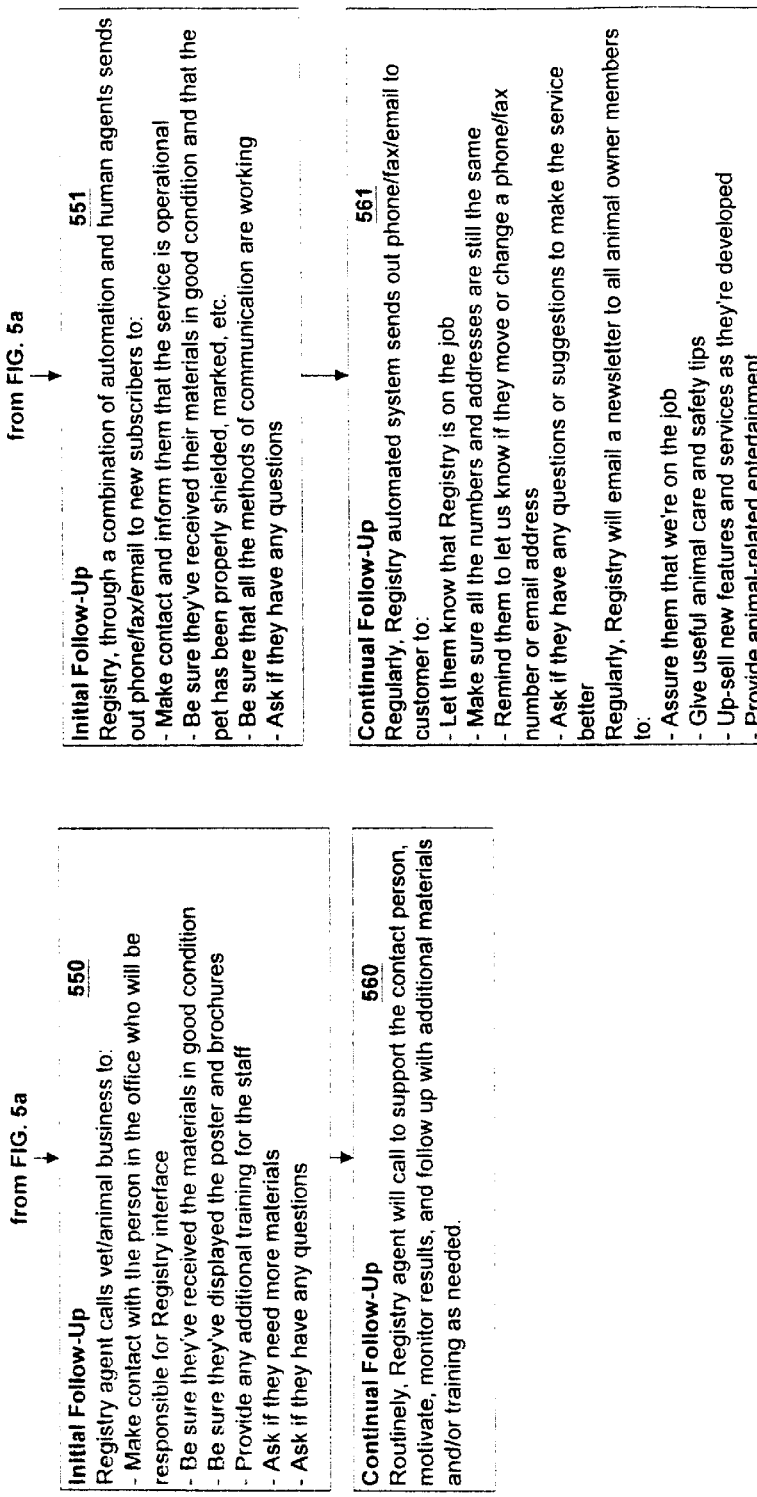

FIGS. 5a and 5b illustrate the detailed logic flow of the preferred embodiments of enrollment for each of a veterinarian/animal business and registration of an animal by its owner.

B.3.1 VETERINARIAN/ANIMAL BUSINESS ENROLLMENT PROCESS (illustrated in the lefthand column of FIGS. 5a and 5b) comprises the following steps:

a. Marketing 500—Marketing is conducted at trade shows and conferences, through local groups, at various professional and group meetings, on a veterinarian-to-veterinarian basis, through animal business-to-animal business referrals, and through print, on-line, broadcast, and via owners of registered animals acting as vendor/marketers to owners of non-registered animals and via a sales force and via the Registry System itself using the Communication Methods.

b. Decision To Enroll as Vendor/Marketer 510—Initially, most veterinarians and animal business owners enroll at conferences or trade shows to offer the Registry System to animal owners. Additionally, veterinarians and animal business owners may complete an enrollment form received through marketing channels or the mail or via facsimile or other Communication Methods in which case the enrollment form would be returned to the Registry System by mail or facsimile or other Communication Methods or otherwise. Enrollment may also be accomplished by completing a form at a Web Site or by calling an inward toll free telephone number and providing the necessary information.

c. Information Check 520—The Registry System checks each vendor/marketer enrollment form for completeness. If necessary due to incomplete or incorrect information being provided on an enrollment form, the Registry System notifies a Registry System representative to contact a proposed enrollee to obtain additional information.

d. Verification 530—When a form appears to be complete, a Registry System automated agent or human representative contacts the enrollee to verify the enrollment form information.

e. Receipt of Starter Package 540—A starter package is provided to each veterinarian and animal business enrollee which starter package comprises the Registry System member handbook, terms of service, license, training materials, display materials, referral brochures, and information on incentives available to the enrollee's staff who register animal owner clients of the Registry System.

f. Initial Follow-up 550—Shortly after the distribution of the starter package to a vendor/marketer, a Registry System agent contacts the business office of the veterinarian enrollee or animal business vendor/marketer to establish contact with the responsible party in the office, to make sure the starter package materials have been received in good condition and understood, to make sure the appropriate materials (e.g., posters and brochures) are displayed, to answer questions, to arrange for additional training as requested, and to provide any additional materials which may be needed or requested.

g. Continuing Follow-up 560—Periodically after the initial contact, a Registry System agent calls the responsible party in the business office of the veterinarian enrollee or animal business enrollee to offer additional training and materials, monitor results, provide motivation to promote and use the Registry System, and maintain current contact information with respect to the veterinarian and animal business.

B.3.2 Animal Owner Registration Process (illustrated in the righthand column of FIGS. 5*a*–*b*) comprises the following steps:

a. Marketing 501—Marketing is conducted at animal shows and breeder conferences, through local groups, at various non-profit organization meetings, through veterinarian to animal owner referrals, through animal business-to-animal owner referrals, and through print, on-line, broadcast, and other media and the Communication Methods. Marketing is two-fold: (1) to vendor/marketers, and (2) to animal owners.

b. Decision To Register 511—Most animal owners may decide to register their animals(s) with the Registry System by using a registration form received at a veterinarian's office. Additionally, animal owners may complete a registration form received through various marketing channels or the mail or via facsimile in which case the registration form is returned to the Registry System by mail or facsimile. Registration may also be accomplished by completing a form at a Web Site or by calling an inward toll free telephone number and providing the necessary information or by the Communication Methods.

c. Information Check 521—The Registry System checks each registration form for completeness. If necessary, due to incomplete or incorrect information being provided on a registration form, the Registry System notifies a Registry System representative to contact a proposed registrant to obtain additional information.

d. Verification 531—When a form appears to be complete, a Registry System automated agent or human representative contacts the registrant to verify the registration form information.

e. Receipt of Starter Package 541—A starter package is provided to each animal owner registrant, which starter package comprises the Registry System member handbook, terms of service, referral brochures, and information concerning fees for animal owners who register other animal owners in the Registry System, and at least one Information Unit or Shield to be carried by the registered animal.

e. Initial Follow-up 551—Shortly after the distribution of the starter package to an animal owner registrant, a human or automated Registry System agent contacts the registrant to address issues comprising confirmation that the starter package materials have been received and understood, that the Information Unit or Shield has been installed on the animal and is working, provision of any additional training or information needed, confirmation (in the case of a transmitting and/or receiving shield) that communications are working properly, and answering any questions. In addition the Registry System performs regularly scheduled tests of its interaction and interface with all Communication Methods.

f. Continuing Follow-up 561—Periodically, after the initial post-enrollment contact, the Registry System performs follow-up activities comprising sending an automated message via phone, facsimile, e-mail, and/or regular mail to each animal owner to obtain current information for the Registry Database(s), to ask for feedback concerning the Registry System services, to offer animal safety tips, to sell new features and services, and to re-offer existing services the animal owner initially declined to purchase.

B.4 Incident Reporting

Figure 6A:
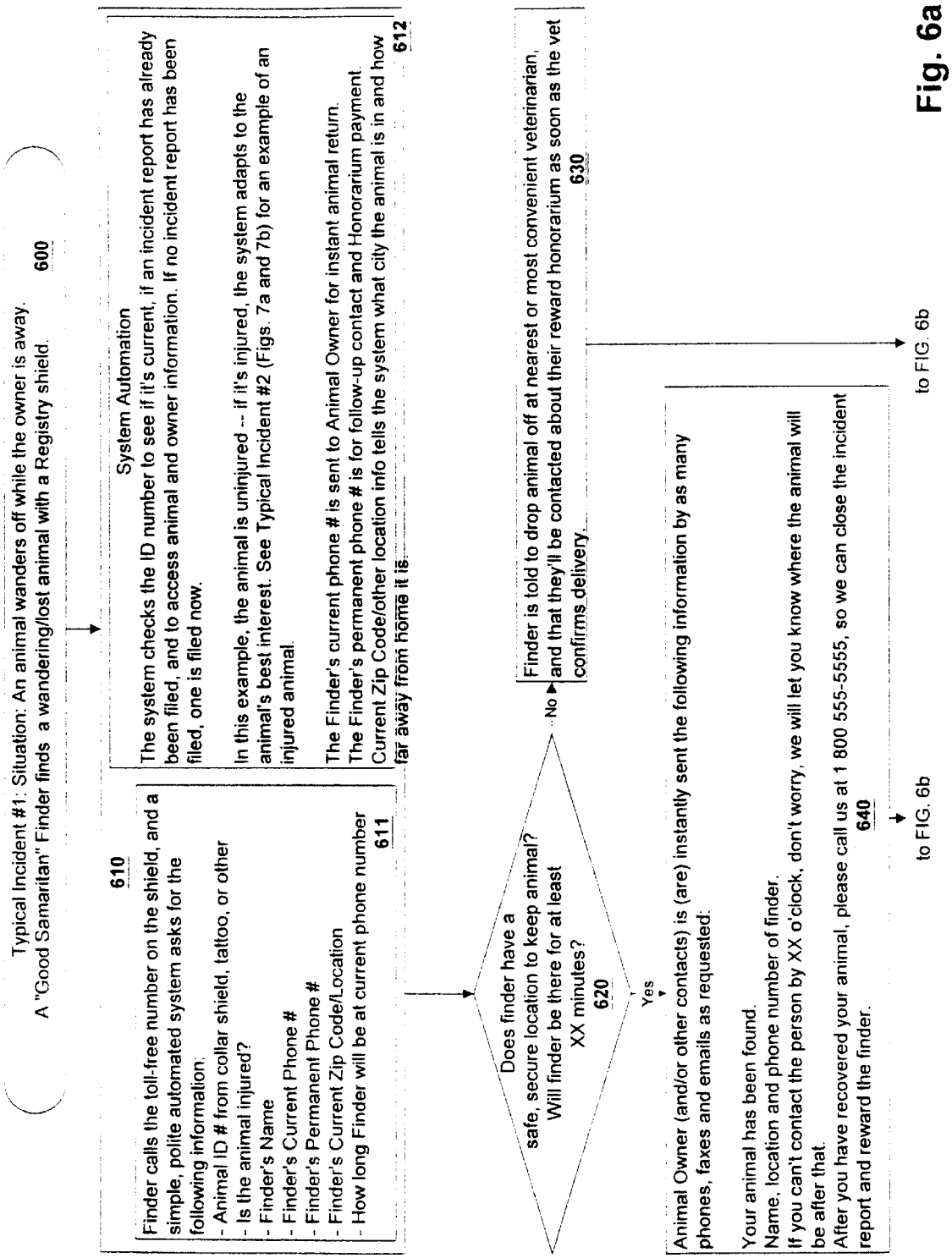
FIGS. 6a–b illustrate a preferred embodiment of an incident report made to the Registry System by an animal finder.
Figure 6B:
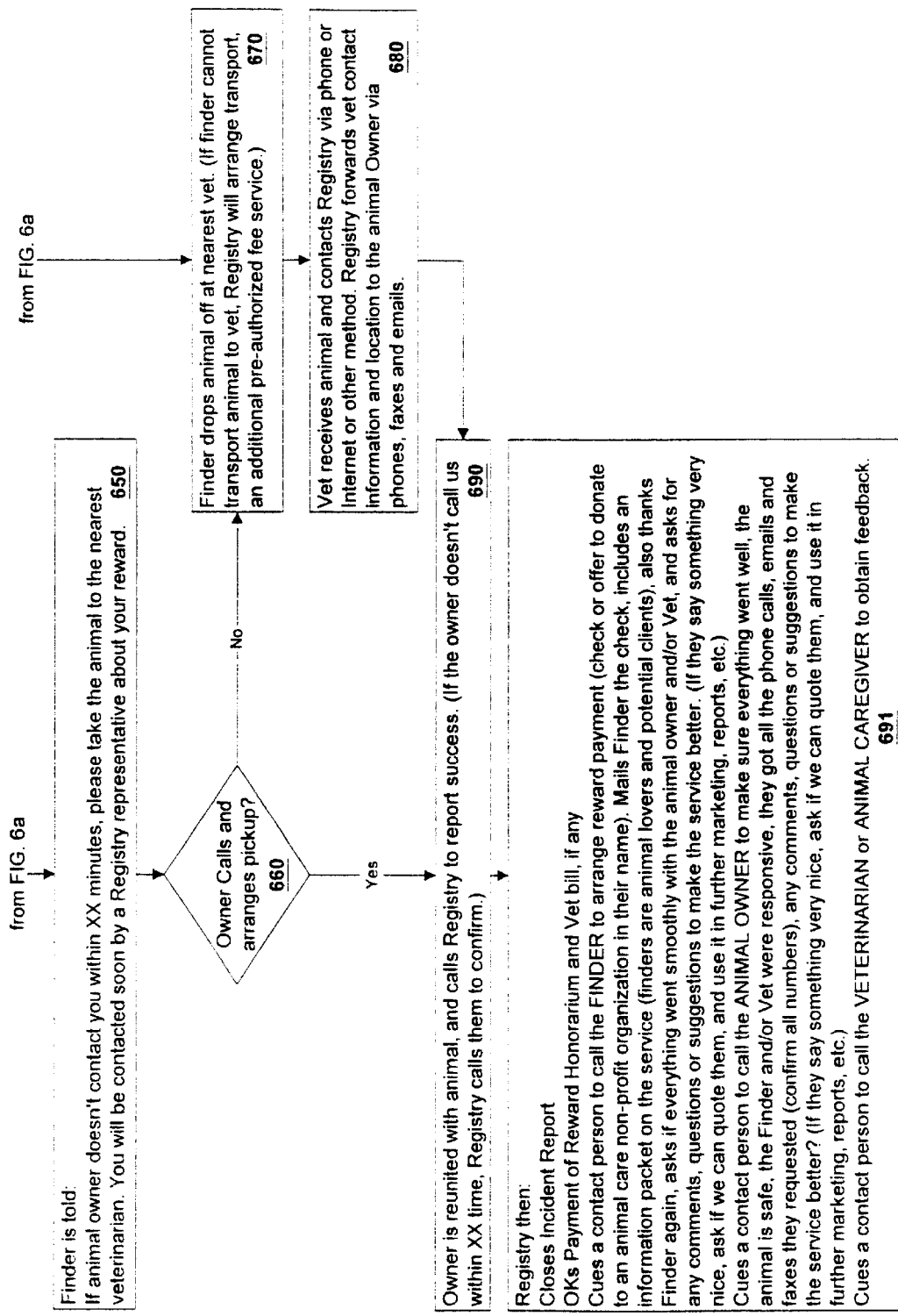
Figure 7A:
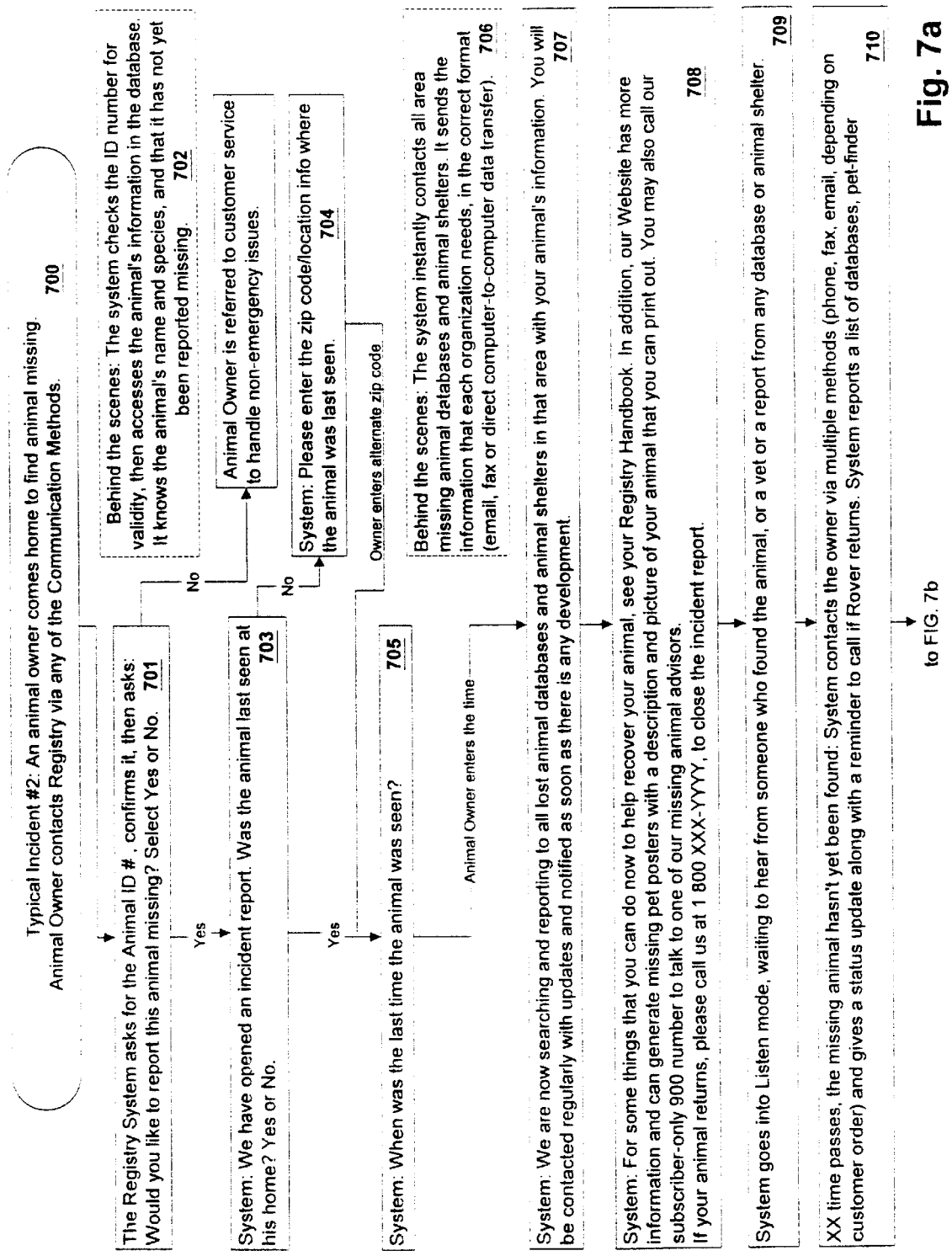
FIGS. 7a–b illustrate a preferred embodiment of an incident report made to the Registry System by an animal owner.
Figure 7B:
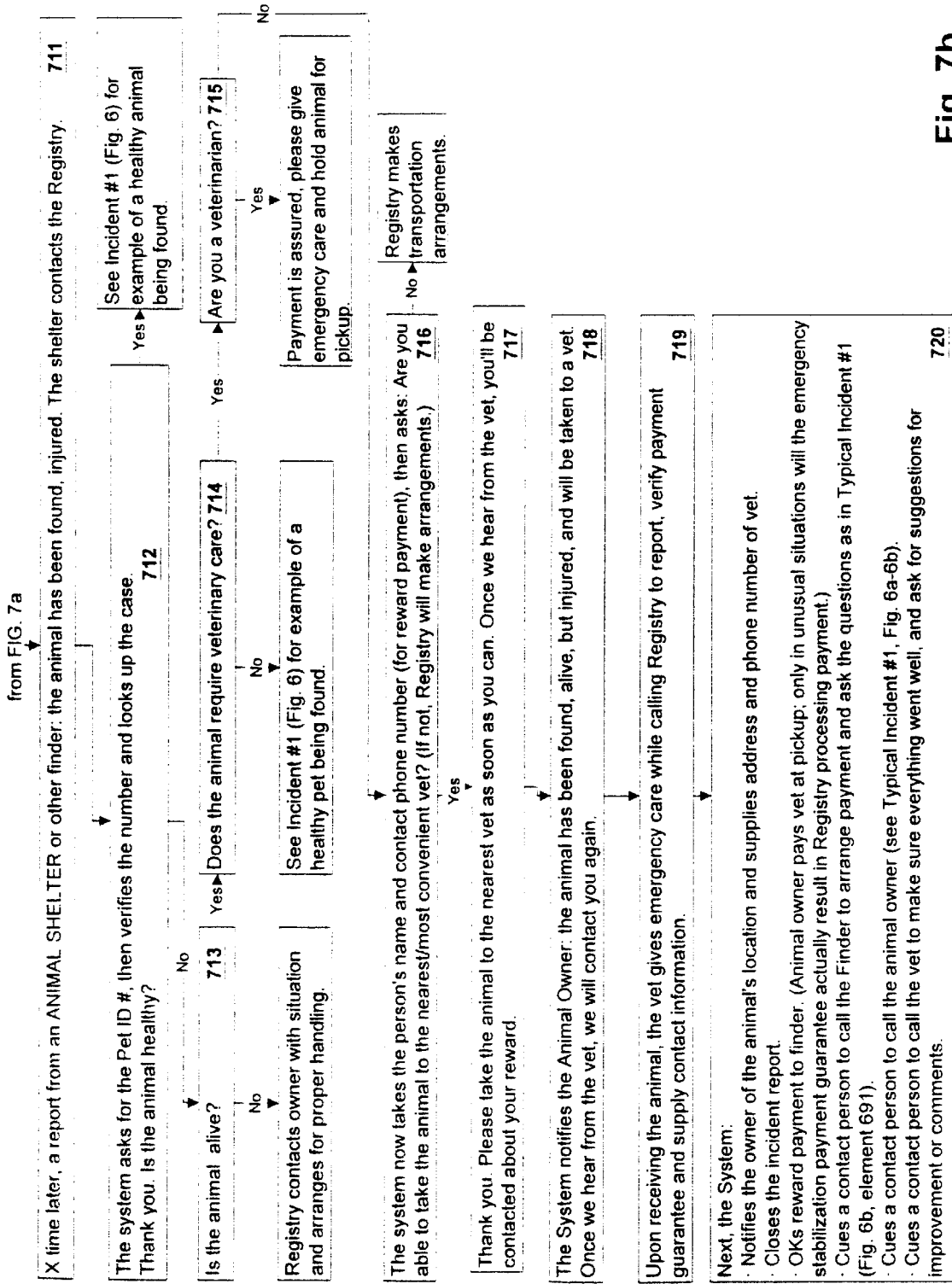

FIGS. 6*a* and 6*b* illustrate preferred embodiments of the processing associated with an incident report when a third party finds a missing registered animal. FIGS. 7*a* and 7*b* illustrate preferred embodiments of the processing associated with an incident report when an animal owner discovers that a registered animal is missing.

B.4.1 Third Party Finds Missing Animal (FIGS. 6*a* and 6*b*)

When an animal wanders away or is somehow lost without the owner's knowledge and a third party finder (e.g., a Good Samaritan) finds 600 the animal bearing a Registry System Information Unit or Shield and contacts the Registry System 611, in a preferred embodiment the Registry System's interaction with the finder comprises the following steps:

a. Finder calls inward toll free telephone number—The Registry System automatically solicits 611 the animal identification code, the animal's condition, the finder's contact information and validates 612 the animal identification code as identifying a currently registered animal, determines 612 if there is a missing animal incident report and if not files one, if the animal is injured the system adapts 612 to the animal's best interest, and creates 612 a record of the finder's information in Registry Database(s).

b. Registry System finds a safe haven for animal until pickup—The Registry System determines 620 if the finder can hold the animal for pickup and if so contacts 640 the animal owner for pickup. If 650 the finder can not hold the animal for pickup or if the animal owner does not pick up the animal, then the finder is directed 630 to deliver the animal to the nearest or most convenient veterinarian or the Registry System arranges 670 for animal transportation to the veterinarian. After the veterinarian receives 680 the animal dropped off by the finder, the veterinarian contacts 680 the Registry System that notifies 680 the animal owner of the veterinarian's location and contact information and confirms payment arrangements c. Owner arranges pickup—If the owner calls and arranges 660 to retrieve the animal, the owner is reunited with the animal and the owner contacts 690 the Registry System to report success.

d. Closeout incident—When the Registry System receives a success report, it closes the incident report and authorizes 691 payment of any reward.

e. Follow up—After an incident report is closed, the Registry System also contacts 691 the finder, animal owner, and veterinarian or animal caregiver to obtain their feedback about the incident and the Registry System's response and to solicit testimonials, if appropriate, which can be used in marketing.

In this preferred embodiment the, Registry System uses technology when it works better than humans (e.g. direct computer-to-computer communication when time is of the essence) and uses humans when they work better than electronic systems (e.g., to obtain feedback and testimonials after an incident report is closed).

B.4.2 Animal Owner Discovers Animal Missing (FIGS. 7a and 7b)

FIGS. 7a and 7b illustrate the Registry System processes when an animal owner finds an animal missing and the animal owner contacts the Registry System. In a preferred embodiment, the Registry System's interaction with the animal owner comprises the following steps:

a. Animal Owner calls inward toll free telephone number—The animal owner contacts 700 the Registry System via Communication Methods or the inward toll-free Registry System emergency telephone number contained in the Registry System Starter Package.

b. The Registry System solicits information—

(1) The Registry System automatically asks 701 if the caller wants to report a missing animal, obtains the animal's Registry System identification code, and then validates the identification code 702. If the caller does not want to report a missing animal, he caller is referred to customer service to handle non-emergency issues.

(2) The Registry System opens an incident report and solicits 703, 704, 705 when and where the animal was last seen.

c. Interface to external animal databases—The Registry System sends 706 a copy of the incident report to external animal databases near where the animal was last seen and advises 707 the animal owner that external databases have been notified.

d. Provide animal owner with actions—The Registry System automatically provides 708 the animal owner with a list of actions the animal owner can take to help recover the lost animal, provides a number for the animal owner to call to talk with a counselor, and reminds the animal owner to contact the Registry System if the animal returns. Actions comprise obtaining over the Internet for local printout preformatted posters with animal photo, media advertisements, mailing labels for the area surrounding the location where the animal was lost, paper doorknob hanging notices, shelter or Society for the Prevention of Cruelty to Animals or database notification to reinforce Registry System notifications, and post cards with animal photo and owner contact information imprinted thereon.

e. Registry System listens for reports—The Registry System enters 709 the Listen mode to await a found animal report and sets 709 a timer which initiates periodic contact with the animal owner to contact the animal owner with updated information while the animal is missing and to assure the animal owner that the Registry System is actively seeking return of the missing animal.

f. Timer expires—The Registry System automatically contacts 710 the animal owner with updates concerning which databases and organizations have been sent a lost animal report and reminds the animal owner to contact the Registry System if the animal returns.

g. Found animal report—The Registry System receives 711 from a finder a report that the animal has been found.

h. Information input for found animal—The Registry System validates 712 the animal identification code. If the animal is healthy, the call and the animal are handled as set forth in FIGS. 6a and 6b for an animal which is found in good health. If the animal is not healthy, the Registry System determines the animal's status.

j. Next action determination—The Registry System determines 713 if the animal is alive, determines 714 if the animal needs medical care and determines 715 if the caller is a veterinarian. The Registry System then takes 716 contact information from the caller and makes 717 arrangements to deliver the animal to a veterinarian with the assistance of the caller. If the caller is not able to transport the animal to a veterinarian, the Registry System optionally arranges transportation to a veterinarian. If the animal is not alive, the Registry System optionally contacts the owner with the information and makes further arrangements with the owner concerning handling of the animal's remains.

k. Close out of incident report—The Registry System notifies 718 the animal owner that the animal has been found and is being taken to a veterinarian. When the animal arrives at the veterinarian's office, the veterinarian provides 719 reception, holding, and/or stabilizing medical care as necessary, reports to the Registry System that the animal has arrived, and provides contact information and verifies that payment is made for service rendered. The Registry System notifies 720 the owner of the location and telephone number of the veterinarian caring for the animal, closes the incident report, authorizes payment of any reward to the finder, and directs a contact person to obtain feedback concerning the incident and the response of the Registry System from the finder, the animal owner, and the treating veterinarian 691.

Figure 8:
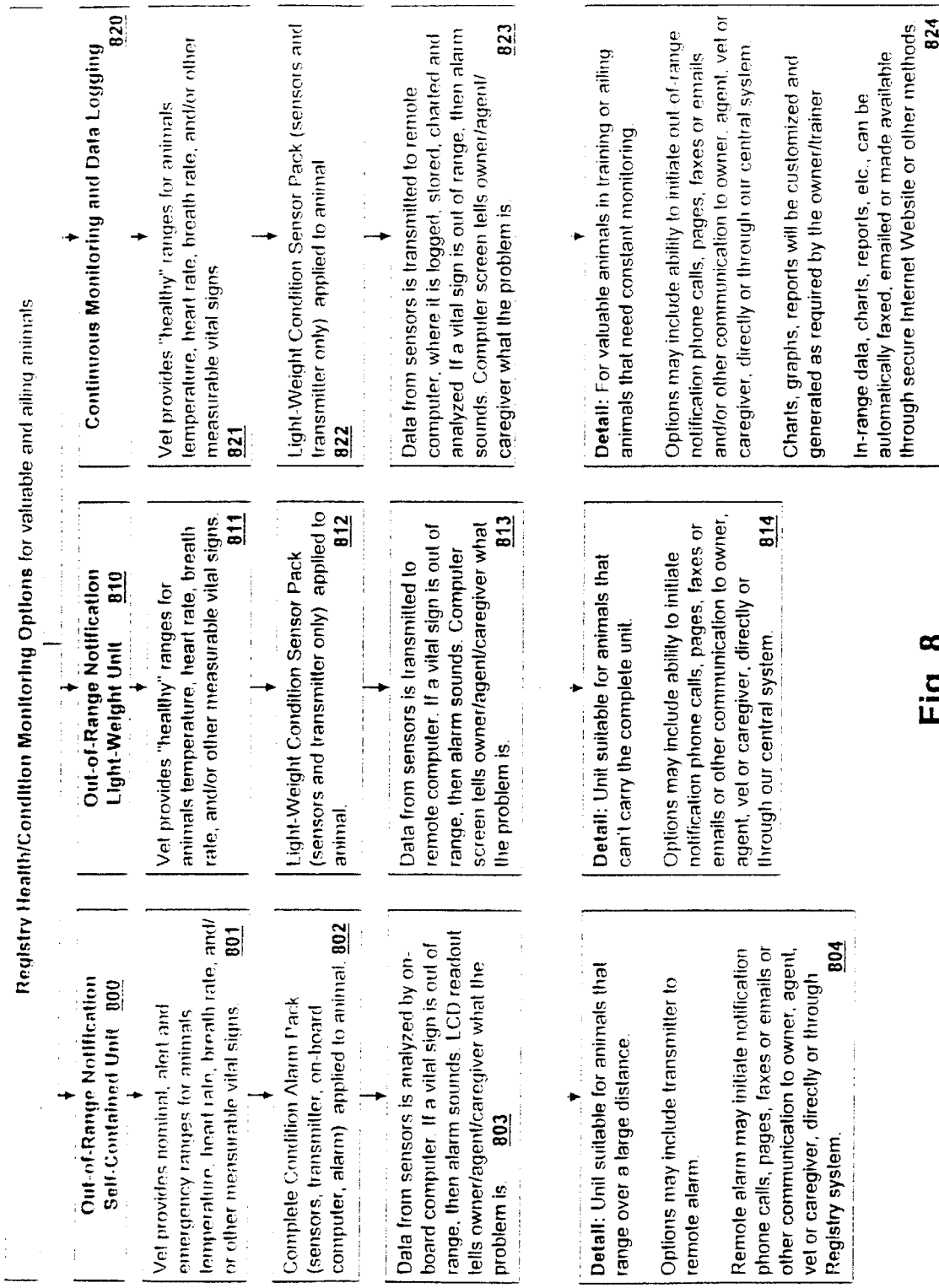
FIG. 8 illustrates preferred embodiments of health/condition monitoring options of an Information Unit or Shield.

FIG. 8 illustrates various animal health/condition monitoring levels.

(i) Out-of-Range (Self-Contained) Unit 800—In connection with an Out-of-Range (Self-Contained) Unit 800, a veterinarian designates 801 ranges for various health indicators (temperature, heart rate, respiration rate, for example) comprising nominal, alert, and emergency ranges for the type of animal being monitored. A Complete Condition Sensor Pack (which comprises measurement sensors, a transmitter/receiver, an on-board computer, a liquid crystal display (LCD), and an alarm) is applied 802 to and/or in the animal to monitor and process conditions in the designated ranges. When the on-board computer monitoring the indicators detects that a monitored indicator is out-of-range, a visible read-out on the liquid crystal display (LCD) provides 803 the owner with an alarm and information about the out-of-range health indicator. In an alternative embodiment, the Unit 800 may transmit to a remote alarm system which may initiate an alarm notification using the Communication Methods to the owner/representative or a veterinarian or through the Registry System 804;

(ii) Out-of-Range Notification (Light-Weight) Unit 810—In connection with an In-Health/Out-of-Health Range (Light-Weight) Unit 810, a veterinarian designates 811 ranges for various health indicators (temperature, heart rate, respiration rate, for example) comprising nominal, alert, and emergency ranges for the type of animal being monitored. A Light-Weight Condition Sensor Pack (which comprises measurement sensors and a transmitter) is applied 812 to the animal to monitor conditions in the designated ranges. The measurements from the sensors are transmitted to a remote computer for processing. When the remote computer monitoring the indicators detects that a monitored indicator is out-of-range, a visible read-out on the display screen associated with the remote computer provides 813 the owner with an alarm and information about the out-of-range health indicator. In an alternative embodiment, the Unit 810 may directly initiate (or transmit to a remote alarm system which may initiate) an alarm notification comprising telephone calls, pages, faxes, notification of owner/representative or a veterinarian which occurs when any device fails, and/or e-mails directly to the owner or a veterinarian or through the Registry System 814 all of which occur via the Communication Methods; and (iii) Continuous Monitoring and Data Logging 820—In connection with Continuous Monitoring and Data Logging 820 an Out-of-Range (Light-Weight) Unit 810 is used and a veterinarian designates 821 ranges for various health indicators (temperature, heart rate, respiration rate, for example) comprising nominal, alert, and emergency ranges for the type of animal being monitored. A Light-Weight Condition Sensor Pack (which comprises measurement sensors and a transmitter) is applied 822 to the animal to monitor conditions in the designated ranges. The measurements from the sensors are transmitted via the Communication Methods to a remote computer for processing. When the remote computer monitoring the indicators detects that a monitored indicator is out-of-range, a visible read-out on the display screen associated with the remote computer provides 823 the owner with an alarm and information about the out-of-range health indicator. The remote computer logs, stores, charts, and analyzes the measurement data from the sensors on the animal. These features may be of particular value in connection with the training of animals or in connection with caring for ailing animals. Custom charts, graphs, and reports can be produced to meet the specifications of the animal owner or animal trainer. Further, in-range data or any measured data can be automatically sent by facsimile or e-mail or other Communication Methods or made available through secure Internet Website connections or by other means of data transmission. In an alternative embodiment, the Unit 810 may directly initiate (or transmit to a remote alarm system which may initiate) an information alert or an alarm notification comprising telephone calls, pages, faxes, and/or e-mails 824 directly or via other Communication Methods to the owner/representative or a veterinarian or through the Registry System.

FIG. 9 illustrates various animal shield service levels.

i. Standard Shield 900—The steps in the use of the standard shield or tattoo system 900 are as follows: In the first step an animal wanders away from home 901. When an animal wanders away from home 901, this shield or tattoo 900 provides a unique identifier for the animal and an indication of the Registry System inward toll free telephone number and web address 902. The animal's location is reported 903 verbally or on-line via the Web so that Registry System computers can record the report 904 and inform the owner of the report 905;

ii. Passive Alarm Shield 910—The steps in the use of the Passive Alarm Shield 910 are as follows: In the first step, the animal wanders 911 outside the designated "safe" area. When an animal leaves 911 a designated "safe" area, this shield sets off an alarm 912 comprising a beep or siren, "Go Home" voice command, or other verbal command, or alarm 913. The alarm can additionally trigger a telephone call, fax or email to at least one of the owner, owner's agent/representative, and the Registry System 914;

iii. Active Voice Shield 920—The steps in the use of the Active Voice Shield 920 are as follows: In the first step, an animal bearing this type of shield 920 wanders outside a designated "safe" area 921 (an area designated either by physical or electronic markers or by a given radius from a central location). Then, an alarm sounds 922, and a voice recording soliciting help is broadcast 923 or, in an alternative embodiment, the alarm can be activated by the owner if the animal wanders outside the designated area 924;

iv. Tracking Shield 930—The steps in the use of the Tracking Shield 930 are as follows: In the first step, an animal wanders 931 outside a designated area (an area designated either by physical or electronic markers or by a given radius from a central location). When an animal bearing this type of shield wanders 931 outside the designated "safe" area, a homing signal 932 is transmitted by the shield and the owner can track the animal to the animal's location with a device such as a mobile receiver/antenna 933 or, in an alternative embodiment, the alarm can be activated 934 by the owner if the animal wanders outside the designated area.

v. GPS Locator Shield 940–The steps in the use of the GPS Locator Shield 940 are as follows: In the first step, an animal bearing this type of shield wanders 941 outside a designated "safe" area. Then the GPS Locator Shield calculates 942 the exact location of the animal using signals transmitted by the Global Positioning Satellite system. The calculated location is forwarded 943 to the owner and/or the Registry System so the owner is able to track 944 the animal's location on one or more of a map on a computer, a laptop computer, a personal digital assistant (PDA), or other device capable of interfacing with the GPS Locator Shield. The GPS Locator Shield combines a portable GPS transmitter/receiver and a voice transmitter comprising a 2-way radio, cell phone or custom device.

The Registry System has many different reactions and question paths, depending on the situation and only a few possibilities have been discussed in these two preferred embodiments. Registered animals can be taken to any veterinarian and the veterinarian is assured payment. Vendor/marketer participation by the veterinarian in the Registry System is not required. The animal owner is kept informed on a current and continuing basis and the owner may intervene in the pre-established process at any point.

It should be noted that the term "animal" with respect to the Registry System and method of the present invention comprises companion animals, livestock, thoroughbred horses, any other animals that can be lost, be stolen, and stray from their owner's possession or control.

The description and examples are intended to illustrate and not to limit the scope of the invention which is defined by the full scope of the appended claims and which invention is entitled to protection within the full scope of the appended claims.

It is appreciated by persons skilled in the art that the present invention is not limited to what has been particularly shown and described herein. Rather, the scope of the present invention is defined only by the claims that follow:

What is claimed is:

1. A computer enabled system for storage of information about an individual animal for dissemination thereof at a time of an incident report made by a member or a non-member of the system concerning said animal to facilitate at least one response to said incident report, said system comprising:

a plurality of predetermined incident report types each having at least one predetermined response type;

means for communicating between said system and at least one selected from the group consisting of a member and a non-member;

at least one database that stores information about the individual animal that determines said at least one predetermined response to an incident report of a given type;

at least one type of Information Unit or Shield that contains an animal identification code associating said individual animal with said stored information about said individual animal;

a care registry system for receipt and response to said at least one type of incident report for said individual animal bearing said at least one Information Unit or Shield, wherein said response includes at least one of (1.) pre-authorization of at least one of care, holding or reception services for said individual animal; (2.) pre-authorization of payment for said at least one of care, holding or reception services for said individual animal; (3.) authorization of at least one of care, holding or reception services for said individual animal; and (4.) authorization for payment of at least one of care, holding or reception services for said individual animal, wherein, each said type of incident report comprises said animal identification code contained in the Information Unit or Shield that is used to access stored information about an individual animal such that the stored information determines the at least one predetermined response.

2. The system of claim 1, wherein:

said animal identification code comprises a unique sequence of one or more juxtaposed components selected from the group consisting of numbers 0–9, letters, and single character symbols; and said Information Unit or Shield contains said animal identification code.

3. The system of claim 1, wherein said plurality of predetermined incident report types comprises at least one selected from the group consisting of missing animal, found animal, sighted animal, cared-for animal, received animal, injured animal, healthy animal, and stolen animal.

4. The system of claim 3, wherein a found animal incident report comprises an identification of a finder and said pre-determined response type optionally includes a reward for said finder.

5. The system of claim 1, wherein when said incident report concerns a found animal and said at least one predetermined response is notifying the animal's owner.

6. The system of claim 1, wherein said at least one database comprises at least one each of the database types selected from the group consisting of the types animal, owner, owner's agent, owner's associate, incident, veterinarian, animal business, animal control officer, animal welfare organization, animal welfare person, animal care professionals, and accounting.

7. The system of claim 1, further including a means for bearing said at least one said Information Unit or Shield selected from the group consisting of tattoo, brand, tag attached to animal, transmitting device attached to animal, identifying device attached to animal, transmitting device inserted under skin of animal, identifying device inserted under skin of animal, transmitting device swallowed by animal, identifying device swallowed by animal, transmitting device borne by the animal, identifying device borne by the animal, transceiving device borne by the animal, receiving device borne by the animal, and speaking device borne by the animal.

8. The system of claim 1, wherein said Information Unit or Shield communicates said unique identifier of the animal bearing it and at least one set of information about the animal bearing it selected from the group consisting of vital signs, location, medical history and conditions, description, conditions in proximity of animal, authorization for veterinary reception, holding, care and payment, and optionally outputs at least one audible message over a speaker borne by the animal.

9. The system of claim 1, wherein said means for receipt and response to said at least one incident report comprises:

receipt of said incident report by a communications method selected from the group consisting of registrant contact tree, non-registrant contact tree, and the following communication methods and technologies: telephone, wireless device, Internet website, Internet, broadcast television, cable television, fiber optic equipment, computer, pager, facsimile, cell phone, two-way radio, FM radio, AM radio, short wave radio, microwave device, U.S. Postal Service, private postal service, private delivery service, private messenger, e-mail equipment, PDA (Personal Digital/Data Assistant), telephony, other Internet equipment, other Website equipment, code, and satellite.

10. A computer enabled system for storage of information about an individual animal for dissemination thereof at a time of an incident report concerning said animal to facilitate at least one response to said incident report, said system comprising:

a plurality of predetermined incident report types each having at least one pre-determined response type;

at least one database that stores information about the individual animal that determines said at least one predetermined response to an incident report of a given type;

at least one type of Information Unit or Shield that contains an animal identification code associating said individual animal with said stored information about said individual animal;

a registry system for receipt and response to said at least one type of incident report for said individual animal bearing said at least one Information Unit or Shield, wherein said response includes at least one of pre-authorization of services, pre-authorization of payment for said services; authorization of services; and authorization for payment of services for said individual animal, wherein, each said type of incident report comprises said animal identification code contained in the Information Unit or Shield that is used to access stored information about an individual animal such that the stored information determines the at least one predetermined response and wherein said services comprise at least one of reception, holding and care of said individual animal; further comprising:

means for registering owners of animals and their animals, wherein, said at least one database further comprises information about the registered owners and their animals;

means for enrolling veterinarians, animal businesses, animal control officers, associates of animal control officers, animal welfare organizations, animal welfare persons, animal care professionals, animal detectives, and private investigators; wherein, said at least one database further comprises information about enrolled veterinarians, animal businesses, animal control officers, associates of animal control officers, animal welfare organizations, animal welfare persons, animal care professionals, animal detectives, and private investigators; and wherein, said pre-determined response types further comprise notification to an owner of said animal of the incident report or sending said animal to any veterinarian or animal care facility or animal care person located near a location of said animal for at least one of the services selected from the group consisting of reception, holding, and treatment.

11. The system of claim 10, wherein:

said registered owners solicit and register non-registered animal owners and optionally receive a fee for each registration; and said enrolled veterinarians enroll non-enrolled veterinarians and optionally receive a fee for each enrollment that optionally exceeds a pre-determined threshold; and said enrolled businesses register animal owners and enroll animal businesses and optionally receive a fee for each registration and enrollment that exceeds a pre-determined threshold.

12. The system of claim 10 wherein the registry system uses the stored information to offer animal related, and optionally non-animal related, goods and, optionally, services to individuals and, optionally, organizations about whom information is stored in the system.

13. The system of claim 1, wherein said pre-authorized payment is at least one of the types selected from the group consisting of credit card, debit card, charge account, bank draft, cash, cash deposits, wire transfer, animal insurance and electronic funds transfer wherein the system optionally maintains a charge account for the owner of each registered animal.

14. The system of claim 1, further comprising:

concierge services comprising at least one of counselors available to help owners launch a missing animal campaign, counselors to help with the emotional stress, counselors to help with the emotional loss, pickup of found animal, satellite or other tracking of lost animals, animal's vital sign determination and transmission to designated recipient, animal private investigation, bond to counter unlawful actions against registered animal, reward for recovery of animal, transport of animal, attendant for animal, entertainment of animal, relaxation of animal, exercise of animal, search and rescue for animal, access to animal and care for animal during owner's disability, access to animal and care for animal during owner's absence, arranging and guaranteeing payment for care for an animal during and following an emergency in the structure where the animal usually lives, 900 number type bill-to-caller telephone services, 800 number type inward toll-free telephone services, and communication to animal owner of notices designated as noteworthy by the registry system;

wherein, a charge on a per concierge service basis is made.

15. The system of claim 1, wherein said pre-determined response comprises communication of the incident to at least one recipient selected from the group consisting of animal shelter, humane society, animal control officer, rescue organization, other animal information systems, and other systems.

16. The system of claim 1, wherein said Information Unit or Shield provides at least one of the location/tracking options selected from the group consisting of standard identifying code shield/tattoo/brand, passive alarm, active voice, tracking, and GPS locator, transmitter, and receiver.

17. The system of claim 16, wherein said Information Unit further comprises a health/condition monitoring unit selected from the group consisting of in-range out-of-healthy range notification, self-contained unit, in-range out-of-healthy range notification light-weight unit, and a continuous monitoring and data logging unit.

18. The system of claim 1 wherein there is at least one link between the registry system and an emergency monitoring and alarm organization.

19. A computer implemented method for recovery and monitoring of animals, comprising the steps of:

providing a plurality of incident report types each having at least one predetermined response type;

providing a unique animal identification code for an individual animal;

storing information using said unique animal identification code for an individual animal and a corresponding predetermined response for each of said plurality of incident report types for dissemination thereof at a time of receipt of one of said incident report types concerning the animal;

providing an Information Unit or Shield that contains an animal identification code thereupon that associates an animal with the stored information about the animal;

bearing the provided Information Unit or Shield by the animal identified thereon by the contained animal identification code;

receiving one of said plurality of incident report types comprising the animal identification code contained on an Information Unit or Shield borne by the animal; and responding to said received incident report with said predetermined response type for said received incident report type that comprises the animal identification code and with at least one of (1.) pre-authorization of at least one of care, holding or reception services for said individual animal; (2.) pre-authorization of payment of at least one of care, holding or reception services for said individual animal; (3.) authorization of at least one of care, holding or reception services for said individual animal; and (4.) authorization of payment for said at least one of care, holding or reception services for said individual animal.

20. The system of claim 1, wherein said care comprises veterinary care.

* * * * *